US011773143B2

(12) United States Patent
Dubois et al.

(10) Patent No.: US 11,773,143 B2
(45) Date of Patent: Oct. 3, 2023

(54) CONFORMATIONAL EPITOPES IN RESPIRATORY SYNCYTIAL VIRUS G PROTEIN CENTRAL CONSERVED REGION

(71) Applicants: Trellis Bioscience, LLC, Menlo Park, CA (US); The Regents of the University of California, Oakland, CA (US)

(72) Inventors: Rebecca Dubois, Santa Cruz, CA (US); Stas Fedechkin, Santa Cruz, CA (US); Lawrence M. Kauvar, San Francisco, CA (US)

(73) Assignees: Trellis Bioscience, LLC, Redwood City, CA (US); The Regents of the University of California, Oakland, CA (US)

( * ) Notice: Subject to any disclaimer, the term of this patent is extended or adjusted under 35 U.S.C. 154(b) by 80 days.

(21) Appl. No.: 16/159,497

(22) Filed: Oct. 12, 2018

(65) Prior Publication Data
US 2019/0135876 A1    May 9, 2019

Related U.S. Application Data

(60) Provisional application No. 62/633,999, filed on Feb. 22, 2018, provisional application No. 62/588,022, (Continued)

(51) Int. Cl.
*C07K 14/135* (2006.01)
*A61P 31/14* (2006.01)
(Continued)

(52) U.S. Cl.
CPC ............ *C07K 14/135* (2013.01); *A61K 39/12* (2013.01); *A61K 39/155* (2013.01); *A61P 31/14* (2018.01);
(Continued)

(58) Field of Classification Search
None
See application file for complete search history.

(56) References Cited

U.S. PATENT DOCUMENTS

| | | | | |
|---|---|---|---|---|
| 7,736,648 B2* | 6/2010 | Kauvar | ................... | A61P 31/12 424/147.1 |
| 8,173,131 B2* | 5/2012 | Tripp | ..................... | A61P 37/04 424/159.1 |

(Continued)

FOREIGN PATENT DOCUMENTS

| | | |
|---|---|---|
| JP | 2000512136 | 9/2000 |
| JP | 2007505033 | 3/2007 |

(Continued)

OTHER PUBLICATIONS

Manning et al. Stability of Protein Pharmaceutical: An Update. Pharmaceutical Research, vol. 27, No. 4, Apr. 2010 (Year: 2010).*

(Continued)

*Primary Examiner* — Michelle S Horning
(74) *Attorney, Agent, or Firm* — FisherBroyles, LLP; Jason M. Pass

(57) ABSTRACT

X-ray crystallography has defined conformational properties of a key functional region of the G protein of respiratory syncytial virus (RSV). Mimics of these epitopes have utility as immunogens, as tools for discovery of antibodies and other monoclonal binding agents, and as pharmacological agents to modulate activity of the host receptors for this viral protein.

9 Claims, 2 Drawing Sheets

Specification includes a Sequence Listing.

Related U.S. Application Data filed on Nov. 17, 2017, provisional application No. 62/572,271, filed on Oct. 13, 2017.

(51) Int. Cl.
```
    A61K 39/155    (2006.01)
    C07K 14/005    (2006.01)
    A61K 39/12     (2006.01)
    C07K 16/10     (2006.01)
    A61K 39/00     (2006.01)
```

(52) U.S. Cl.
CPC ........ *C07K 14/005* (2013.01); *C07K 16/1027* (2013.01); *A61K 2039/552* (2013.01); *C12N 2760/18522* (2013.01); *C12N 2760/18533* (2013.01); *C12N 2760/18534* (2013.01)

(56) References Cited

U.S. PATENT DOCUMENTS

| | | |
|---|---|---|
| 2004/0009177 A1 | 1/2004 | Tripp |
| 2005/0042230 A1 | 2/2005 | Anderson |
| 2006/0018925 A1 | 1/2006 | Tripp |
| 2013/0034564 A1 | 2/2013 | Kauvar |
| 2019/0055545 A1* | 2/2019 | Elledge .............. C12N 15/1037 |

FOREIGN PATENT DOCUMENTS

| | | |
|---|---|---|
| WO | 1997046581 | 12/1997 |
| WO | 2005007189 | 1/2005 |
| WO | 2012006395 | 1/2012 |

OTHER PUBLICATIONS

Collarini et al. Potent High-Affinity Antibodies for Treatment and Prophylaxis of Respiratory Syncytial Virus Derived From B Cells of Infected Patients. J Immunol. Nov. 15, 2009; 183(10): 6338-45. (Year: 2009).*

Scheiblhofer et al. Influence of protein fold stability on immunogenicity and its implications for vaccine design. Expert Rev Vaccines. May 2017;16(5):479-489. doi: 10.1080/14760584.2017.1306441. Epub Mar. 24, 2017. (Year: 2017).*

Fedechkin, S. et al., "Conformational Flexibility in Respiratory Syncytial Virus G Neutralizing Epitopes." J Virol. Feb. 28, 2020; 94(6):e01879-19.

Fedechkin, S. et al., "Structures of respiratory syncytial virus G antigen bound to broadly neutralizing antibodies." Sci Immunol. Mar. 9, 2018 ;3(21):eaar3534.

Jorquera, P., et al., "Respiratory syncytial virus: prospects for new and emerging therapeutics." Expert Rev Respir Med. Aug. 2017; 11(8):609-615.

Jorquera, P., et al., "Understanding respiratory syncytial virus (RSV) vaccine development and aspects of disease pathogenesis." Expert Rev Vaccines. 2016; 15(2):173-87.

Tripp, R., et al., "Respiratory Syncytial Virus: Targeting the G Protein Provides a New Approach for an Old Problem." Journal of virology vol. 92, 3 e01302-17. Jan. 17, 2018.

Communicaton pursuant to Rule 164(1) EPC, Partial Supplementary Search Report, issued in EP18865711.8 dated Jun. 21, 2021.

Murata et al., "Humoral response to the central unglycosylated region of the respiratory syncytial virus attachment protein", Vaccine. Aug. 31, 2010;28(38):6242-6. doi: 10.1016/j.vaccine.2010.07.011. Epub Jul. 23, 2010.

Youngjoo et al., "Antibodies to the central conserved region of respiratory syncytial virus (RSV) G protein block RSV G protein CX3C-CX3CR1 binding and cross-neutralize RSV A and B strains", Viral Immunol. Jun. 2012;25(3):193-203. doi: 10.1089/vim.2011.0094. Epub May 2, 2012.

Jorquera et al., Layer-by-layer nanoparticle vaccines carrying the G protein CX3C motif protect against RSV infection and disease, Vaccines, 2015, 3, 829-849.

Zhang et al., Vaccination to induce antibodies blocking the CX3C-CX3CR1 interaction of respiratory syncytial virus G protein reduces pulmonary inflammation and virus replication in mice, Journal of Virology, 2010, 84(2) 1148-1157.

* cited by examiner

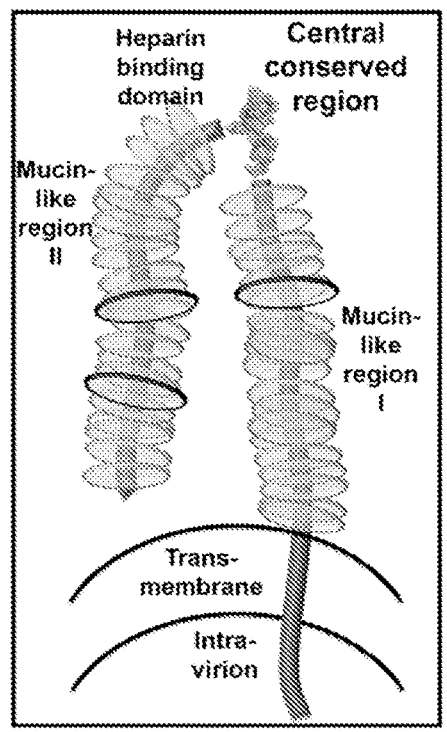 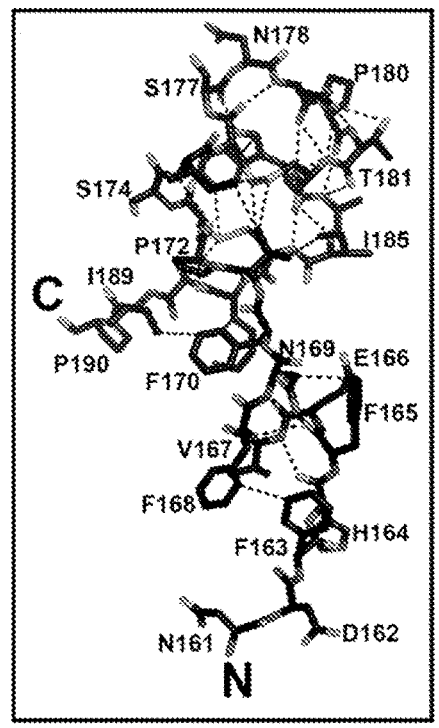
FIG. 1A  FIG. 1B
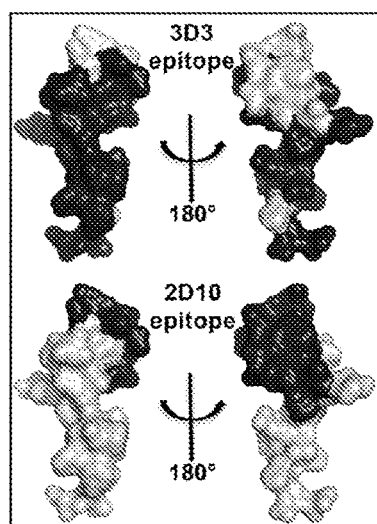 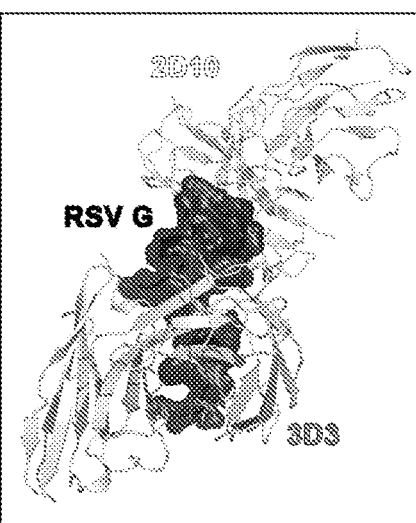 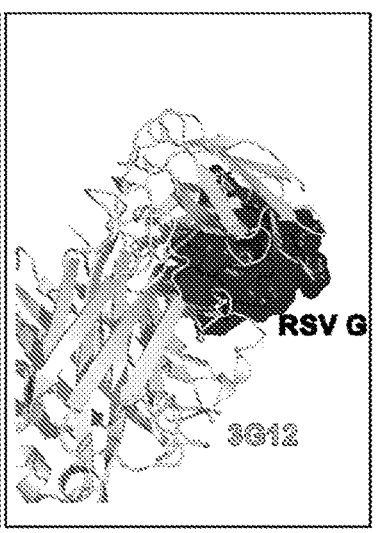
FIG. 2A  FIG. 2B  FIG. 2C

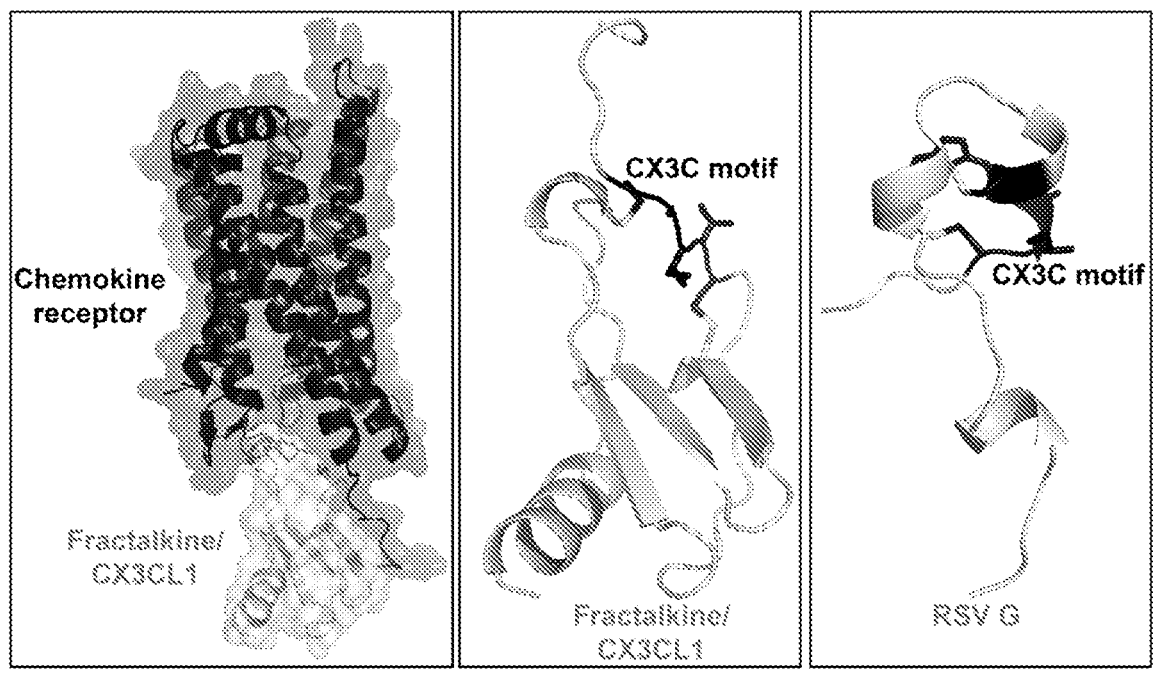
FIG. 3A  FIG. 3B  FIG. 3C
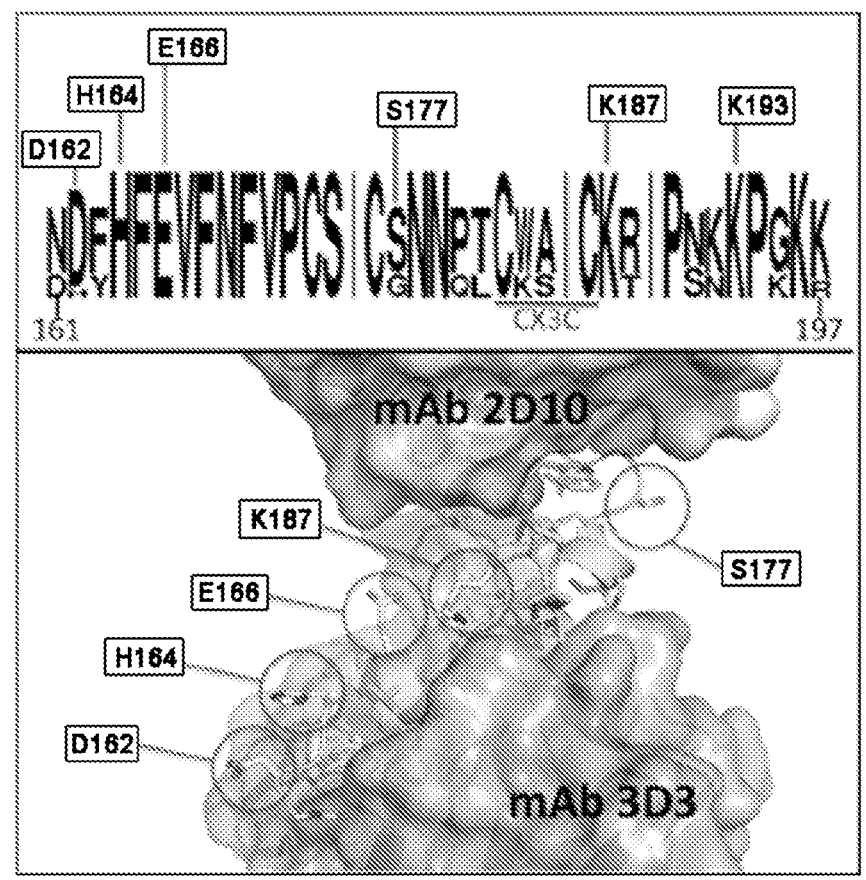
FIG. 4A
FIG. 4B

CONFORMATIONAL EPITOPES IN RESPIRATORY SYNCYTIAL VIRUS G PROTEIN CENTRAL CONSERVED REGION

CROSS-REFERENCE TO RELATED APPLICATIONS

This application claims benefit of U.S. Application Ser. No. 62/572,271 filed 13 Oct. 2017, U.S. Application Ser. No. 62/588,022 filed 17 Nov. 2017 and U.S. Application Ser. No. 62/633,999 filed 22 Feb. 2018. The contents of the above patent applications are incorporated by reference herein in their entirety.

INCORPORATION BY REFERENCE OF SEQUENCE LISTING

The present application is being filed along with a Sequence Listing in electronic format. The Sequence Listing is provided as a file entitled 388512013700SeqList, which was created Oct. 12, 2018 and is 17,500 bytes in size. The information in the electronic format of the Sequence Listing is incorporated by reference in its entirety.

FIELD OF THE INVENTION

In general, the field of the invention is the treatment of infectious disease. More specifically, the field is prophylaxis and treatment of respiratory syncytial virus (RSV) infection. Epitopes of broadly neutralizing monoclonal antibodies defined by high resolution structural analysis enable design of optimized immunogens and screening tools for discovery of treatments. Further, the field includes treatment of defective host immune function by mimicry of respiratory syncytial virus.

BACKGROUND ART

RSV is a negative-strand RNA virus with 10 genes encoding 11 proteins, which has resisted effective management for over 60 years in part because infection does not provide robust immunity {Broadbent, L. et al. Influenza Other Respir Viruses (2015) 9:169-78}. To date, no vaccine has been approved despite several substantial attempts {Jorquera, P. A. and Tripp, R. A. Expert Rev Respir Med (2017) 11(8):609-615}. Over 50% of infants in the US are infected during their first year, with nearly 5% requiring hospitalization {American Academy of Pediatrics Committee on Infectious Diseases, American Academy of Pediatrics Bronchiolitis Guidelines. Pediatrics (2014) 134:e620-38}. Severe RSV disease in infancy is an established risk factor for childhood asthma-like symptoms {Gelfand, E. W. Curr Opin Immunol (2012) 24(6):713-9}. The only care available for RSV infection is supportive. Preterm infants (<29 weeks gestational age) have been the focus for prophylaxis with a humanized mouse mAb (palivizumab, marketed by MedImmune as Synagis®), an expensive treatment which reduces morbidity but not mortality {Meissner, H. C. and Kimberlin, D. W. Pediatrics (2013) 132:915-8}. Palivizumab has not been shown to be safe and effective for post-infection treatment {Malley, R. et al. J Infect Dis (1998) 178:1555-61}. Global incidence of RSV infection in young children is less well documented than in the US but is believed to be more than double that of US, with higher mortality rates {Nair H., et al. Lancet (2010) 375(9725):1545-1555}. In addition, up to 12% of medically attended acute respiratory illness in older adults is attributed to RSV infection with 6-8% of these cases being lethal. Hospitalizations last 3 to 6 days, with a substantial fraction admitted to the intensive care unit {Colosia, A. D., et al. PLoS ONE. (2017) 12(8): e0182321}. RSV infections are also common in immunocompromised patients with mortality of over 25% {Shah, D. P., et al. Blood (2014) 123(21):3263-3268}.

RSV has two major surface glycoproteins, F and G. The sole marketed mAb against RSV (Synagis®, described above) is only approved for prophylactic use in premature infants, and is directed against the F protein. This mAb is broadly useful due to conservation of the F protein sequence among strains. By contrast, the G protein overall is quite variable, although a region in the middle of the sequence is highly conserved. Two subtypes of RSV, A and B, circulate alternately at ~1-2-year intervals, with comparable incidence worldwide.

Initial attempts at prophylaxis for RSV by vaccination with formalin-inactivated RSV proved counterproductive, leading to enhanced disease and pulmonary eosinophilia {Kim, H. W., et al. Am J Epidemiol (1969) 89:422-434}. U.S. Pat. No. 8,173,131 discloses compositions that include the CX3C chemokine motif in the RSV G protein for prevention and treatment of RSV infection, both as interfering agents for modulating RSV infection by tying up the relevant receptor or for inducing immunity. This motif is required for successful infection by RSV {Jeong, K. I., et al. PLoS One (2015) 10(6):e0130517}. U.S. Pat. No. 8,846,056 discloses immunogenic peptides from RSV G protein as vaccine components, specifically including residues 164-176 or 155-206. U.S. Pat. No. 9,321,830 discloses mAbs useful in treating RSV infections that bind to conserved linear sequences of the G protein of RSV in the region including residues 167-176; as these antibodies were derived from the natural human immune repertoire, they are expected to be minimally immunogenic when administered to a human subject. About 15% of the RSV G protein is secreted due to use of an alternative translation start site at codon 48 that eliminates the cytoplasmic domain and a portion of the transmembrane domain region {Hendricks, D. A., et al. J Virol (1988) 62:2228-33}. Deletion of this start site considerably reduces virulence {Stobart, C. C., et al. Nat Commun (2016) 7:13916}, {Arnold, R., et al Virology (2004) 330:384-397}. This is significant since high affinity for antigen is needed for neutralizing soluble factors {Tabrizi, M., et al. AAPS J (2010) 12:33-43}, and therefore mAbs with low pM affinity such as those disclosed in U.S. Pat. No. 9,321,830 are advantageous.

Collarini, E. J., et al. J Immunol (2009) 183:6338-45 describes high affinity, broadly neutralizing mAbs that bind to the RSV G protein central conserved region (CCR) as well as antibodies with varying affinities including 3D3 (1.1 pM), 2B11 (10 pM), 3G12 (580 pM), 5D8 (4.4 nM). The epitopes defined by these mAbs are of particular interest since human antibodies are particularly favorable from both an efficacy perspective (having been cloned from healthy donors) and a safety perspective (reduced chance of off-target reactivity that would create toxicity). The mAb 3D3 has shown broad neutralizing activity both in vitro and in rodent models; the epitope for 3D3 defined at the level of short linear peptides is highly conserved across nearly all circulating strains. An additional mAb, 2D10, is of interest since no linear peptide epitope could be defined for it although it is active in viral neutralization assays in vitro, albeit with lower potency than 3D3 {U.S. Pat. No. 8,273, 354}. These antibodies as well as 3G12 are employed in determining the utility described above.

The contents of these documents and all documents cited herein are incorporated herein by reference.

A recombinant fusion protein comprising the central region (residues 131-230) of the G proteins of both RSV A and B subtypes was shown to be an effective immunogen in mice {Lee, J. Y. and Chang, *J. PLoS One* (2017)12: e0175384}. A G protein peptide, residues 148-198 emulsified in DMSO and PBS, has also been tested in mice as an immunogen and found to be effective at inducing antibodies that both neutralize infection and block G protein binding to CX3CR1 {Choi, Y., et al. *Viral Immunol* (2012) 25(3):193-203}. Similarly, vaccination with nanonparticles that incorporate the G protein residues 169-198 induced protection in mice challenged with RSV {Jorquera, P. A., et al. *PLoS One* (2013) 8:e74905}. Fine scale optimization of peptides from this region has also been attempted, with insertion of one extra residue into the G protein at residues 182-186 greatly reducing the deleterious effects of G protein on the host immune response {Boyoglu-Barnum, S., et al. *J Virol* (2017) 91(10) pii: e02059-16}.

Although these results are encouraging, no RSV G protein vaccine has been approved. Repeated infection is common for this virus, unlike many others. The immunosuppressive properties of the G protein may be responsible for this effect. Criteria defining quality of an immunogen, for which further improvements are useful, include: uniformity of response (titer and affinity) across a diverse human population; stability (particularly important for use in countries lacking an effective refrigerated supply chain); specificity (active against all circulating strains), and safety (in particular, lack of deleterious pharmacological activity on the CX3C chemokine receptor); and duration of response. Design of improved vaccine components is one of the aspects of the present invention, based ultimately on interaction of conformational epitopes of the G protein with antibodies of known affinity.

Despite the important role of the RSV G protein in RSV infection and disease, almost no structural information has been described for this protein. Only the NMR solution structure of the 16 amino acid RSV G cysteine noose has been determined {Sugawara, M., et al. *J Pept Res* (2002) 60:271-282}.

DISCLOSURE OF THE INVENTION

The structures of peptides from the CCR of the G protein complexed with mAbs 3D3, 2D10 and 3G12 have now been determined at high resolution by x-ray crystallography and establish that amino acids 161-197, (SEQ ID NO:1) that includes the key functional region of RSV G, is located at the apex of the G glycoprotein, rendering it accessible to antibody binding.

The present invention relates to compositions related to epitopes on the G protein from respiratory syncytial virus (RSV) revealed by crystallographic studies of high affinity, broadly neutralizing monoclonal antibodies (mAbs) bound to peptides derived from the conserved central region (CCR) of the G protein that is known to interact with host cell factors. These compositions include peptides and other binding moieties that mimic specifically portions of the central conserved region (CCR) of the G protein that also includes a region that is known to interact with host cell factors, including the CX3C receptor (CX3CR1). More specifically, RSV G protein is organized as an N-terminal cytosolic region, a transmembrane region, and a variable ectodomain consisting of two mucin-like domains separated by a non-glycosylated central conserved region (CCR). The CCR contains four cysteine residues that form a cysteine noose, formed by disulfide bonds between a.a. 173-186 that further comprises a cystine loop at a.a. 176-182 and a CX3C chemokine motif (a.a. 182-186). Specific peptides or peptidomimetics derived from the epitopes in this region may be used as immunogens or as tools for discovery of binding agents capable of neutralizing RSV. The invention also comprises epitope mimics that accentuate immunogenicity while minimizing pharmacological activity or vice versa.

A deleterious pharmacological activity of a G protein vaccine is interaction with CX3CR1, which leads to undesirable side effects such as inflammation. Peptide-based vaccines that include a functional CX3CR1 binding site may thus stimulate this undesirable result. As shown below, the three dimensional structure of the interaction of G protein with high affinity antibodies permits the identification of conserved residues of the CCR that can be modified to inactivate the CX3CR1 binding site and decrease or obliterate this effect without compromising the immunogenicity of the vaccine. As used herein, "modified peptide" and "mutant" are used interchangeably.

Thus, in one aspect, the invention is directed to mutants of the G protein or of peptides comprising all or a portion of the CCR thereof that are immunogenic but lack the ability to activate CX3CR1. These mutants can be designed by identifying amino acids that are contained within the CCR of the G protein and which do not participate in the binding of high affinity antibodies and substituting for them amino acids with side chains of different shape or size or charge, thus inhibiting the binding of the RSV G mutant to the receptor without interfering with the immunogenicity of the peptide or protein. In particular, the invention is directed to a peptide (including full length RSV G protein) that contains at least one amino acid substitution at position 162, 164, 166, 177, 187, and/or 193 of the RSV G protein and that shows reduced chemotactic activity as compared to wild type RSV G protein.

In another aspect, the invention relates to a peptide having the amino acid sequence of residues 161-197 of respiratory syncytial virus (RSV) G protein (SEQ ID NO:1) or the amino acid sequence of positons 162-172 (SEQ ID NO:2) or of positions 169-198 (SEQ ID NO:3) or of positions 157-197 (SEQ ID NO:4) or of positions 148-197 (SEQ ID NO:5) or of positions 161-191 (SEQ ID NO:6), each chemically stabilized to retain the conformation exhibited upon binding to antibody.

An alternative immunogen is a molecule that comprises at least two covalently linked components, wherein said components are peptides of the amino acid sequence SEQ ID NO:2 and/or the amino acid sequence of SEQ ID NO:3 or wherein each of said components is the corresponding mutant or peptidomimetic of SEQ ID NO:2 and/or SEQ ID NO:3.

Peptide embodiments of the invention such as those that mimic soluble RSV G antigens or peptides that are binding moieties can be prepared recombinantly. Peptides that mimic antigens may thus be generated easily to facilitate comprehensive mutational analysis to identify variants within the CCR that can reduce or enhance immunogenicity or provide activation or inhibition of the CX3CR1 receptor.

In another aspect, the invention provides a mutant or peptidomimetic of the peptide of SEQ ID NO:1, SEQ ID NO:2, SEQ ID NO:3, SEQ ID NO:4, SEQ ID NO:5 or SEQ ID NO:6 that has enhanced immunogenicity as compared to the respective peptide of SEQ ID NO:1, SEQ ID NO:2, SEQ ID NO:3, SEQ ID NO:4, SEQ ID NO:5 or SEQ ID NO:6, including embodiments wherein the conformation of said mutant is chemically stabilized.

In some applications, reduced immunogenicity is advantageous, thus the invention also includes mutant or peptidomimetic of the peptides of SEQ ID NO:1, SEQ ID NO:2, SEQ ID NO:3, SEQ ID NO:4, SEQ ID NO:5 or SEQ ID NO:6 that has reduced immunogenicity as compared to the respective peptide of SEQ ID NO:1, SEQ ID NO:2, SEQ ID NO:3, SEQ ID NO:4, SEQ ID NO:5 or SEQ ID NO:6 including embodiments wherein the conformation of said mutant is chemically stabilized.

Agents that either inhibit or activate the C3XCR1 receptor, but have low immunogenicity can enhance or suppress immune responses generally (including those unrelated to RSV infection). Thus in another aspect the invention is directed to a mutant or peptidomimetic of peptides of SEQ ID NO:1, SEQ ID NO:3, SEQ ID NO:4, SEQ ID NO:5 or SEQ ID NO:6 that stimulates or inhibits the chemokine receptor CX3CR1 responsive to fractalkine, especially, wherein this mutant or peptidomimetic has reduced immunogenicity as compared to the respective peptide of SEQ ID NO:1, SEQ ID NO:3, SEQ ID NO:4, SEQ ID NO:5 or SEQ ID NO:6. A suitable in vitro functional analysis interaction of a candidate moiety of the host chemokine receptor CX3CR1 is also disclosed.

Also disclosed is a method for assessing fidelity of test compounds such as peptidomimetics and mutant peptide variants to the disclosed conformational epitope. The method includes measuring the relative binding strength of the peptidomimetics or mutants to mAbs that vary in affinity for the native protein. Agents that bind preferentially to mAbs with high affinity for the native protein are more likely to induce such antibodies than agents that preferentially bind to mAbs with weaker affinity or that have weak affinity for the optimal mAb.

Thus another aspect of the invention is a method to identify immunogens useful in vaccines which method comprises contacting a candidate molecule with mAb 3D3, mAb 2D10 or mAb 3G12 or an antigen-binding fragment thereof and with at least one binding moiety that binds with low affinity to the RSV G protein, whereby a candidate molecule that preferentially binds to 3D3, mAb 2D10 or mAb 3G12 is identified as having said desirable properties as an immunogen. The invention also includes molecules thus identified which may be aptamers or members of a combinatorial library of small molecules or of peptides.

In yet another aspect, the conformational epitope mimics, whether recombinant peptides or peptidomimetics, provide useful tools for discovery of homogeneous compositions of non-immunoglobulin binding moieties with activity similar to the known broadly neutralizing mAbs. Thus the invention includes a method to identify a binding moiety that has the characteristics of strain independence, high affinity for the conserved region of the RSV G protein and neutralizing activity which method comprises contacting a candidate binding moiety with a conformationally restrained form of a peptide having the amino acid sequence of any one of SEQ ID NOs:1-6 as shown in FIGS. 2A-C or a peptidomimetic said restrained form and detecting the presence or absence of a complex between said candidate binding moiety and said peptide or peptidomimetic, wherein the presence of said complex that shows a binding affinity of the candidate binding moiety for said peptide or peptidomimetic at least as strong as 100 pM identifies said binding moiety as having said characteristics. The invention also includes binding moieties thus identified.

The invention further includes methods to provide prophylactic or therapeutic treatment with respect to RSV infection in a subject which method comprises administering to a subject in need of such treatment pharmaceutical or veterinary composition including the immunogens or binding moieties of the invention. The invention also includes methods to treat immune mediated inflammatory diseases, chronic pain and peripheral neuropathy which method comprises administering to a subject in need of such treatment compounds of the invention that interact with the C3XC receptor. These, too, may be included in pharmaceutical or veterinary compositions.

BRIEF DESCRIPTION OF THE DRAWINGS

FIG. 1A-B illustrate the RSV G protein and its central conserved region (CCR). FIG. 1A is a diagram of the prominent location of the CCR at the tip of a folded back structure of the RSV G protein, preceding the heparin binding domain. The CCR structure [residues 161-190] is shown in FIG. 1B at higher resolution, with dotted lines showing non-covalent interactions in the structure, with N and C terminal ends of the region noted.

FIG. 2A-C illustrate the contact regions for mAbs 3D3, 2D10 and 3G12 on the CCR of RSV G protein. FIG. 2A shows front and back views of the CCR as space filling model; black areas are the mAb contact regions. FIG. 2B shows the mAb 3D3 and 2D10 variable domains as ribbon models, and the CCR of RSV G as space filling model. FIG. 2C shows the mAb 3G12 variable domains as ribbon models, and the CCR of RSV G as space filling model. In FIG. 2B-C, the CCRs are aligned at the cysteine noose residues. mAbs 3D3 and 3G12 bind to many of the same amino acids, however the three-dimensional epitopes are very different due to different conformations of the CCR in each structure.

FIG. 3A-C illustrate the structure of fractalkine, the natural ligand for the CX3C chemokine receptor 1. FIG. 3A shows the orientation of fractalkine binding to the receptor. FIG. 3B shows fractalkine, with the CX3C motif in black. FIG. 3C shows a portion of the RSV G protein [residues 161-190] with the CX3C motif in black.

FIGS. 4A and 4B illustrate RSV G CCR (161-197, SEQ ID NO:1). FIG. 4A is a sequence logo showing highly conserved amino acids that may play a role in CX3CR1 binding and activation (height of the single amino acid abbreviations at each residue is proportional to how conserved it is). The location of the CX3C motif is underlined, confirming that the site is not highly conserved by sequence although it does play a significant role in determining the three dimensional conformation. FIG. 4B is a high magnification view of the region bound by mAbs 3D3 and 2D10. Conserved amino acids outside of the mAb epitopes are selected for mutagenesis.

MODES OF CARRYING OUT THE INVENTION

For the first time, high resolution structural data have been obtained for the interaction of high affinity, broadly neutralizing monoclonal antibodies (mAbs) and peptides derived from the conserved central region (CCR) of RSV G protein. These results provide a foundation for rational engineering of an immunogen as has been shown for other viruses {Sharon, J., et al. *Immunology* (2014) 142(1):1-23}. The novel structures define two neighboring conformational epitopes on RSV G CCR, that include helices, disulfide bonds, and polar and hydrophobic interactions between discontinuous amino acids. These results illuminate why linear RSV G epitope peptides and misfolded RSV G are not likely to be fully effective as antigens; for example, an early attempt to target the CCR of the G protein with a recombinant protein vaccine (BBG2Na) showed only a moderate ability to induce neutralizing antibodies in healthy, young adults and a more recent effort also using recombinant G protein failed to establish efficacy in elderly adults {Rezaee, F., et al. *Curr Opin Virol* (2017) 24:70-78}. Mapping of sequence conservation onto the RSV G structure defines a large three-dimensional region on the RSV surface that is highly conserved.

These conformational features of the disclosed peptides or mutants can be stabilized by use of chemical crosslinkers or non-natural amino acids {Robinson, J. A. *J Pept Sci* (2013) 19(3):127-40}.

As shown in Example 5 the Fab of 3D3 complexed to RSV G[162-172](SEQ ID NO:2) was determined to 2.40 Å-resolution. The RSV G[162-172] peptide contains a short helix and projects several hydrophobic residues, including Phe163, Phe165, Phe168, Phe170 and Pro172, into a ~700 $Å^2$ groove formed by heavy-chain complementarity-determining regions (CDRs) 1, 2, and 3 and light-chain CDRs 1 and 3. Surprisingly, the distal six amino acids of the extended heavy-chain CDR3 formed no molecular contacts with the linear epitope peptide. A larger fragment of RSV G (RSV G[161-197]) (SEQ ID NO:1) was produced in *E. coli* and the structure of that complex determined to 2.40 Å-resolution. Additional interactions with 3D3 included heavy-chain CDR3 contacts with the RSV G cysteine noose (residues 173-186) as well as additional interactions between heavy-chain CDRs 1 and 2 and RSV G residues 189-190. Altogether, 3D3 binds to RSV G at a discontinuous, conformational epitope comprising ~1,060 Å2, designated as antigenic site γ1.

The mAb 2D10 also binds RSV G but its epitope could not be characterized by linear epitope mapping. A recombinant single-chain variable fragment (scFv) of 2D10 forms stable complexes with a synthetic RSV G peptide (RSV G[169-198] SEQ ID NO:3), and as also shown in Example 5 the crystal structure of the complex was determined to 1.56 Å-resolution. The mAb 2D10 uses a twisted heavy-chain CDR3, heavy-chain CDR2, and light-chain CDR3 to bind to a ~550 $Å^2$ epitope on the RSV G cysteine noose. The CX3C chemokine motif, which forms a short helix in the cysteine noose, is buried by 2D10 binding. Although the 2D10 epitope is comprised mainly of residues 177-188, and is thus technically continuous, the cysteine noose comprises two nested disulfide bonds that induce strong conformational character to this epitope, designated as antigenic site γ2.

The three dimensional conformations of the three peptides used for these studies superimpose nearly identically. A diverse set of RSV G sequences was used to map conservation level onto this consensus RSV G structure. Despite overall high variability of full-length RSV G (53% identity between subtypes RSV A and B), the 37 amino acid fragment RSV G[161-197] contains 24 invariant residues (70% identity between subtypes RSV A and B). Notably, in the CX3C motif only one of the three "X" amino acids, Ile185, is highly conserved, implying that this motif alone does not comprise the CX3CR1-binding site, but the invariant cysteines in the CX3C motif stabilize a three-dimensional surface of highly conserved amino acids that form extensive atomic interactions across the entire region. Many aspects of the invention are derived from these findings.

Definitions

Unless defined otherwise, all technical and scientific terms used herein have the same meanings as commonly understood by one of ordinary skill in the art to which this disclosure belongs.

"Protein", "peptide" and "polypeptide" are used interchangeably and to refer to chains of naturally occurring amino acids coupled through amide bonds such that they can be synthesized by recombinant methods regardless of the length of the chain. "Peptidomimetics" include unnatural or synthetic amino acids, including D and L isomers and amino acid analogs linked by amide linkages or other bonds, e.g., ester, ether, etc. "Peptidomimetics" also include organic molecules not obviously analogous to peptides, including, for example, aptamers.

As used herein, "binding moiety" includes antibodies and alternative non-immunoglobulin binding moieties as set forth hereinbelow. "Antibodies" include immunoreactive fragments of traditional antibodies and their various fragmented forms that still retain immunospecificity such as Fab, F(abab₂, F, fragments, single-chain antibodies in which the variable regions of heavy and light chain are directly bound without some or all of the constant regions. Also included as "antibodies" are bispecific antibodies which contain a heavy and light chain pair derived from one antibody source and a heavy and light chain pair derived from a different antibody source. Similarly, since light chains are often interchangeable without destroying specificity, antibodies composed of a heavy chain variable region that determines the specificity of the antibody may be combined with a heterologous light chain variable region. Chimeric antibodies with constant and variable regions derived, for example, from different species are also included.

For the variable regions of mAbs, as is well known, the critical amino acid sequences are the CDR sequences arranged on a framework which framework can vary without necessarily affecting specificity or decreasing affinity to an unacceptable level. Definition of these CDR regions is accomplished by art-known methods. Specifically, the most commonly used method for identifying the relevant CDR regions is that of Kabat as disclosed in Wu, T. T., et al., *J. Exp. Med.* (1970) 132:211-250 and in the book Kabat, E. A., et al. (1983) Sequence of Proteins of Immunological Interest, Bethesda National Institute of Health, 323 pages. Another similar and commonly employed method is that of Chothia, published in Chothia, C., et al., *J. Mol. Biol.* (1987) 196:901-917 and in Chothia, C., et al., *Nature* (1989) 342:877-883. An additional modification has been suggested by Abhinandan, K. R., et al., *Mol. Immunol.* (2008) 45:3832-3839. The mAbs described herein include the CDR regions as defined by any of these systems or other recognized systems known in the art.

The specificities of the binding of mAbs are defined, as noted, by the CDR regions mostly those of the heavy chain, but complemented by those of the light chain as well (the light chains being somewhat interchangeable). Therefore, the mAbs of the invention may contain the three CDR regions of a heavy chain and optionally the three CDR's of a light chain that matches it. Because binding affinity is also determined by the manner in which the CDR's are arranged on a framework, the mAbs may contain complete variable regions of the heavy chain containing the three relevant CDR's as well as, optionally, the complete light chain variable region comprising the three CDR's associated with the light chain complementing the heavy chain in question.

This is true with respect to the mAbs that are immunospecific for a single epitope as well as for bispecific antibodies or binding moieties that are able to bind two separate epitopes.

The invention also includes binding moieties that mimic the binding characteristics of mAbs. mAb mimics include aptamers {Yu, Y., et al. *Int J Mol Sci* (2016) 17(3):358} and protein mimics of antibodies or fragments thereof (alternative scaffolds) such as camelids, anticalins, ankyrin repeat proteins {Azhar A., et al. *Int J Biol Macromol* (2017) 102:630-641}.

Bispecific binding moieties may be formed by covalently linking two different binding moieties with different specificities. Multiple technologies now exist for making a single antibody-like molecule that incorporates antigen specificity domains from two separate antibodies (bi-specific antibody). Suitable technologies have been described by MacroGenics (Rockville, Md.), Micromet (Bethesda, Md.) and Merrimac (Cambridge, Mass.). (See, e.g., Orcutt, K. D., et al., *Protein Eng. Des. Sel.* (2010) 23:221-228; Fitzgerald, J., et al., MAbs. (2011) 1:3; Baeuerle, P. A., et al., *Cancer Res.* (2009) 69:4941-4944). For example, the CDR regions of the heavy and optionally light chain derived from one monospecific mAb may be coupled through any suitable linking means to peptides comprising the CDR regions of the heavy chain sequence and optionally light chain of a second mAb. If the linkage is through an amino acid sequence, the bispecific binding moieties can be produced recombinantly and the nucleic acid encoding the entire bispecific entity expressed recombinantly. As was the case for the binding moieties with a single specificity, the invention also includes the possibility of binding moieties that bind to one or both of the same epitopes as the bispecific antibody or binding entity/binding moiety that actually contains the CDR regions. The invention further includes bispecific constructs which comprise the complete heavy and light chain sequences or the complete heavy chain sequence and at least the CDR's of the light chains or the CDR's of the heavy chains and the complete sequence of the light chains.

In particular, the invention is directed to a mutant or peptidomimetic of a peptide having the amino acid sequence of residues 161-197 of respiratory syncytial virus (RSV) G protein (SEQ ID NO:1) or of positions 169-198 (SEQ ID NO:3), or of positions 157-197 (SEQ ID NO:4), or of positions 148-197 (SEQ ID NO:5), or of positions 161-191 (SEQ ID NO:6) that has diminished activity with respect to activating the chemokine receptor responsive to fractalkine as compared to the respective peptide of SEQ ID NO:1, SEQ ID NO:3, SEQ ID NO:4, SEQ ID NO:5 or SEQ ID NO:6; that binds mAb 3D3, and/or 2D10 and/or 3G12; and/or wherein said mutant or peptidomimetic elicits antibodies immunoreactive with RSV G protein. In some embodiments the elicited antibodies have sub-nM affinity for an epitope of RSV G protein conserved between A and B strains of the virus.

In some embodiments the peptidomimetic or peptide is chemically stabilized to retain the conformation exhibited upon binding to antibody and/or contains at least one substitution for amino acid 162, 164, 166, 177, 187, 192 and/or of 193 the RSV G protein.

In another embodiment the invention includes a mutant or peptidomimetic of peptide of SEQ ID NO:1, SEQ ID NO:3, SEQ ID NO:4, SEQ ID NO:5 or SEQ ID NO:6 that stimulates or inhibits the chemokine receptor responsive to fractalkine as compared to the respective peptide of SEQ ID NO:1, SEQ ID NO:3, SEQ ID NO:4, SEQ ID NO:5 or SEQ ID NO:6. In some embodiments the mutant or peptidomimetic has reduced immunogenicity as compared to the respective peptide of SEQ ID NO:1, SEQ ID NO:3, SEQ ID NO:4, SEQ ID NO:5 or SEQ ID NO:6.

Recombinant Aspects

Any proteins or peptides of the invention may be produced recombinantly using known techniques. The invention also includes nucleic acid molecules comprising nucleotide sequences encoding them, as well as vectors or expression systems that comprise these nucleotide sequences, cells containing expression systems or vectors for expression of these nucleotide sequences and methods to produce the peptides by culturing these cells and recovering the binding moieties produced. Any type of cell typically used in recombinant methods can be employed including prokaryotes, yeast, mammalian cells, insect cells and plant cells. Also included are human cells (e.g., muscle cells or lymphocytes) transformed with one or more recombinant molecules that encode the relevant peptides.

As used herein, "a" or "an" means "at least one" or "one or more."

Activities Based on the CX3C Chemokine Motif

Although variable overall, RSV G (298 residues) contains a ~40 amino acid central conserved region (CCR) that is highly conserved, devoid of glycosylation, and has been shown to play key roles in both virus infection and viral pathogenesis. Specifically, RSV G CCR contains a CX3C chemokine motif that facilitates binding to the human chemokine receptor CX3CR1 to promote RSV infection in human airway epithelial cells as well as modulating signaling that affects trafficking of CX3CR1$^+$immune cells resulting in airway congestion. For example, treatment with mAbs against the CCD of RSV G protein was associated with a reduction in total lung leukocytes in comparison to isotype control treated mice at day 5 post-inoculation, while treatment with anti-F mAb (Synagis) did not reduce total BAL cells {Caidi, H., et al. *Antiviral Research* (2018) 154:149-157}.

There are no structural or sequence similarities between RSV G and fractalkine/CX3CL1, the only known ligand for CX3CR1, aside from the presence of a CX3C motif and its two disulfide bonds, as diagrammed in FIG. 3A-C. In another aspect of the invention, this structural divergence despite similar functionality provides an opportunity to develop therapies that selectively block this interaction, a strategy that led to an antagonist of the HIV co-receptor CCR5 {Lieberman-Blum, S. S., et al. *Clinical Therapeutics* (2008) 30:1228-1250}. Examples of diseases for which selective modulation of CX3CR1 would be beneficial include: immune mediated inflammatory diseases such as rheumatoid arthritis {Szekanecz, Z., et al. *Neth J Med* (2011) 69(9):356-66} and osteoarthritis {Wojdasiewicz, P., et al. *Arch Immunol Ther Exp* (Warsz) (2014) 62(5):395-403}. Atherosclerosis is also now considered to be an inflammatory disease and in animal models blockade CX3CR1 ameliorates disease severity {Apostolakis, S. and Spandidos, D. *Acta Pharmacol Sin.* (2013) 34(10):1251-6}. Chemokines in general, and the natural CX3CR1 ligand (fractalkine) in particular, are also implicated in the peripheral neuropathy thought to underlie chronic pain {Montague, K. and Malcangio, M. *J Neurochem* (2017) 141(4):520-531}. To use the motif as a pharmacological agent, reduced immunogenicity is important to enable repeated administration. De-immunization of the two distinct antibody epitopes thus provides complementary utility to the determination of sites required for pharmacological activity.

Alternatively, enhancement of the activity of the CX3CR1 binding motif can be used to create a novel stimulator of this receptor. This is useful for treating diseases such as ulcerative colitis. In mice, CX3CR1 is implicated in preventing the disease-associated translocation of commensal bacteria to mesenteric lymph nodes. CX3CR1-knockout mice and mice deficient in fractalkine both displayed increased translocation of bacteria and markedly increased disease severity in a model of dextran sulfate sodium (DSS)-induced colitis {Medina-Contreras, O., et al. *J Clin Invest* (2011) 121(12): 4787-95}. In addition, CX3CR1 has been shown to be an important regulator of beta-cell function and insulin secretion {Lee, Y. S., et al. *Cell* (2013) 153(2):413-425}, and the RSV G protein pharmacological motif mimic could thus also be developed as a therapeutic to treat diabetes.

The ability of the stabilized forms of SEQ ID NOs: 1-6 or the mutants or peptidomimetics thereof and their specially constrained forms can be tested for their ability to activate or inhibit the CX3C receptor using, for example, the chemotaxis assay set forth in Example 4 hereinbelow. However, any suitable method for assay could also be used. For use in therapy, it is advantageous for these entities to have relatively low immunogenicity and this too can be tested, for example, using the assays set forth in Example 3, but any suitable test may be used.

Immunogens

Three design goals dominate optimization of a G protein immunogen, each of which is substantially facilitated by the novel structural information.

First, the pharmacological activity of the G protein is deleterious in the context of RSV infection and it is thus preferable to minimize that activity in the immunogen. As noted above, this activity is centered around the C3XC receptor and successful mutants or peptidomimetics can be assessed using the chemotaxis assay, among other assays. The crystallographic studies described in the present invention permit identification of amino acids whose substitution would be useful in diminishing interaction with the C3XC receptor while retaining immunogenic properties which are the second desirable characteristic of a vaccine. Specifically, it has been found that residues 162, 164, 166, 177 and 187 are present in the CCR region of the RSV G protein and/or either a part of or adjacent to the C3XC motif and are not among the residues that specifically bind the high affinity antibodies described herein. Thus, replacing one or more of these residues with an alternative that will either alter the charge or the size and shape of the side chain will interfere with interaction with the C3XC receptor.

Second, high affinity antibodies are needed to neutralize the deleterious soluble G protein produced by virus infected cells, so antibodies generated by the immunogens should have these properties. Affinity can readily be tested using the ELISA assays described in Example 2 or using one of the many alternative methods known in the art. To test for immunogens that will generate antibodies with desirable affinity and neutralization properties, binding to human mAbs that exhibit such desired properties is assessed. As disclosed in Collarini, et al. (supra) mAbs with affinities varying across 3 orders of magnitude, from low pM to low nM: 3D3 (1.1 pM), 2B11 (10 pM), 3G12 (580 pM), 5D8 (4.4 nM) are available for such assays. Candidate immunogens that do not bind well to a high affinity mAb such as 3D3 or 2B11 or that bind better to mAbs with weaker affinity for the natural conformation of the G protein are unlikely to be able to induce production of the desired high affinity mAbs and vice versa.

Third, since RSV is an important pathogen worldwide, including in countries that lack a refrigerated supply chain for delivery of vaccines, stabilization of the immunogen to allow transport and storage at room temperature (or above) is also desirable. Formalin inactivation of live virus, which is effective in other vaccines, is not acceptable for RSV since the first such vaccine caused disease exacerbation upon subsequent natural infection {Kim, H. W., et al. *Am J Epidemiol* (1969) 89:422-34}.

With respect to this third aspect, conformational stability, as has been shown for the RSV F protein, stabilization of the structure via mutations chosen based on antibody-antigen high resolution structural data results in achieving high titer more uniformly across immunized subjects than for the parental virus {McClellan, J. S., et al. *Science* (2013) 340(6136): 1113-1117}. Since the G protein CCR can be made either synthetically or recombinantly, methods well known in the art can be used to systematically mutate this peptide. To facilitate evaluation of a large number of such variants, in vitro assays are needed. Suitable assays are known in the art for mAb binding, for evaluation of thermal stability, and for activation of the CX3CR1 receptor.

In addition to the disadvantage of requirement for refrigeration, the use of flexible peptides as immunogens often elicits antibodies that bind weakly (≥micromolar KD) to conformational epitopes in folded proteins. For that reason, conformationally constrained synthetic epitope mimetics are of particular interest in immunogen design, with examples including efforts addressing HIV, hepatitis C, influenza, and others {Robinson, J. A. *J Pept Sci* (2013) 19(3):127-40}.

Peptides incorporating non-natural motifs are often quite resistant to proteolytic degradation, which is an advantageous feature unrelated to the mimicry itself. A disadvantage of small molecules ("haptens") is that they are often not immunogenic themselves; however, they can become effective immunogens when presented to the immune system embedded in virus like particles {Buonaguro, L., et al. *Exp. Rev. Vaccines* (2011) 10: 1569-1583}.

In particular, the F protein of RSV has been subjected to such mimicry. In this instance, two "staples" (crosslinks) were required to create an effective mimic, which displayed nanomolar potency for inhibition of RSV infection in Hep-2 cells in vitro {Gaillard, V., et al. *Antimicrob Agents Chemother*. (2017) 61(4) pii: e02241-16}.

In addition, constraining the immunogen's three dimensional structure to preserve the high affinity interaction with 3D3 is thus advantageous and a convenient assay is by ELISA binding. Assays for thermal stability known in the literature include observation of increased fluorescence of a dye when bound to hydrophobic sites exposed as the protein unfolds {Biggar, K. K., et al. *BioTechniques* (2012) 53:231-238} and observation of secondary structure character by circular dichroism {Kelly, S. M. and Price, N.C. *Biochim Biophys Acta* (1997) 1338(2):161-185}.

As noted above, methods are available in the art to assess candidate mutants and peptidomimetics for appropriate physiological activity, including evaluation of binding activity and neutralization capability employing antibodies of varying affinity. With respect to constructing candidate mutants and peptidomimetics, the detailed structural information provided by the invention enables targeted mutagenesis to identify the key residues needed for immunogenicity (or for pharmacological activity on the host CX3CR1 receptor noted above to design candidate immunogens). Such "molecular dissection" to separate functions is highly advantageous for identifying product candidates. "De-immunization" (reduction in immunogenicity) has been accomplished for the purpose of enabling repeated administration of a foreign protein {Mazor, R., et al. *Oncotarget* (2016) 7(21): 29916-26}. Purely empirical methods, involving mutating each residue in turn and evaluating the result followed by combinations of such mutations, can be augmented by computational analysis to identify the residues most likely to contribute to immunogenicity and replacements that are most likely to reduce immunogenicity {He, L. and Zhu, J. *Curr Opin* Virol (2015) 11:103-12}. It is already known that insertion of a single additional amino acid within the CX3CR1 motif reduces pharmacological activity {Boyoglu-Barnum, S., et al. *J Virol* (2017) 91(10) pii: e02059-16}. Further determination of inactivating sites enables reduction in this deleterious activity while retaining immunogenicity leading to viral neutralization.

Although the crystal structures described herein have revealed the surface shape and complementarity of mAb interfaces with the RSV G protein CCR, the energetically important interactions are not directly readable from the structures. In other examples of protein-protein interfaces, certain residues constitute 'hot-spots' that make a disproportionately large contribution to binding energy. These privileged sites can be identified by alanine scanning mutagenesis (i.e. creation of variants in which one residue at a time is replaced by alanine) {Robinson, J. A. *J Pept Sci* (2013) 19(3):127-40}; based on the high resolution structure, certain sites will benefit from substituting a different amino acid rather than alanine.

The mAbs 3D3, 2D10, and 3G12 bind quite differently to the same region, as diagrammed in FIG. 2A-C. Thus, de-immunization of each site can be carried out independently. The same process can be used to enhance immunogenicity as well. Optimizing immunogenicity of each site potentially enables a vaccine that comprises a fusion of two or three peptides, among those displaying an optimal immunogen for the 3D3 site, an optimal immunogen for the 2D10 site, and an optimal immunogen for the 3G12 site. Such an immunogen can elicit high affinity mAbs while providing increased resistance to viral escape compared to a single immunogenic site; the avidity boost from two mAbs binding to the CCR (on the same or different copies of the molecule at the virus surface) contributes to higher neutralization potency across the diverse human population. Precedents for such multiple antigen vaccines include an RSV F protein vaccine that incorporates both pre- and post-fusion conformationally stabilized antigens {Cimica, V., et al. *Clin Vaccine Immunol* (2016) 23(6):451-9} and a G protein vaccine that includes residues 131-230 from both A and B strains of RSV {Lee, J. Y. and Chang, J. *PLoS One* (2017)12: e0175384}. Preserving T cell responses, in addition to B cell responses, is also facilitated by the novel structural data; the major T cell epitope has been mapped to residues 185-193 {Varga, S. M., et al. *J Immunol.* (2000) 165(11):6487-95}.

An important aspect of the invention is an effective immunogen for inducing mAbs that block the G protein interaction with CX3CR1, wherein that immunogen itself lacks binding to the receptor. Identifying the residues needed for CX3CR1 binding is accomplished using the same library of variants as for identification of key immunogenic epitopes, but assayed for functionality in a cell based assay for CX3CR1 activation as described in Example 4. Additional variants, such as those that are outside of mAb epitopes but are conserved and predicted to reduce or eliminate CX3CR1 binding, are also useful in this regard. Additional variants, such as insertion of an extra residue in the CX3C motif, may also be candidates.

Development of Alternative Binding Moieties

The conformational epitope mimics, whether recombinant peptides or peptidomimetics, enable efficient discovery of homogeneous compositions of non-immunoglobulin binding moieties with activity similar to the known broadly neutralizing mAbs such as aptamers or alternative scaffolds. Such mimics can provide superior stability, lower cost of manufacture (e.g. by expression in bacterial rather than in mammalian cells), and simpler formulation for inhaled delivery. (The epitope mimics can also be used for identification of additional mAbs.) Homology modeling of the epitope mimics for human RSV can be used to develop analogous epitope mimics for generating mAbs useful in veterinary indications, e.g. to treat bovine RSV infections. Although there is only 30% amino acid identity between the bovine and human RSV G proteins, they share similar features in that the G protein of both viruses has a central conserved cysteine noose region flanked by two more variable domains which are heavily glycosylated {Guzman, E. and Taylor, G. *Mol Immunol* (2015) 66(1):48-56}.

Libraries of such antibody mimics are evaluated by means of competition assays wherein the mimic is used to compete with mAbs such as 3D3, 2D10 or 3G12 for binding to the RSV G protein itself, or more preferably to an epitope mimic that presents the conformational properties in a stable form. Those candidates that successfully compete with the mAb for the epitope are selected as suitable binding agents. Further optimization can be achieved by rank ordering the candidates with regard to binding to epitope mimics that vary in their fidelity to the optimal conformation. As described above with regard to stabilization of epitope mimics, the fidelity of epitope mimics can be determined by measuring relative affinity for mAbs such as 3D3 or mAbs with lower affinity binding to the same general region of RSV G protein. Binding agents are deemed superior if they show stronger affinity for epitope mimics that in turn display high affinity binding to the known mAbs with broadly neutralizing activity.

Applications

The invention is also directed to pharmaceutical and veterinary compositions which comprise as active ingredients the binding moieties, mutants or other peptides or peptidomimetics of the invention. The compositions contain suitable physiologically compatible excipients such as buffers and other simple excipients. The compositions may include additional active ingredients as well, in particular in the case of immunogens immune system stimulants as vaccine adjuvants. The pharmaceutical or veterinary compositions may also contain other formulation excipients, including formulations for intra-nasal or inhaled delivery of mAbs as described in U.S. Pat. No. 9,718,875.

The binding moieties of the invention may also be used in diagnosis.

The immunogens are employed in a method to generate an immune response to RSV, comprising administering formulations containing them to a subject, including a human subject, such as a pregnant woman, an infant, an elderly human, or an immunocompromised subject. The binding moieties of the invention may also be used for therapy or prophylaxis. Infections in other animal species that are related to RSV may also be treated prophylactically or therapeutically by the immunogens or binding moieties of the invention.

Mutants or peptidomimetics that modulate the C3XC receptor are employed in methods to treat other conditions such as rheumatoid arthritis, osteoarthritis, atherosclerosis, diabetes, chronic pain arising from peripheral neuropathy, ulcerative colitis and inflammatory bowel disease.

Example 1: Production of Proteins

A. Production of Fab 3D3 and ScFv 2D10

Recombinant mAbs 3D3 and 2D10 were produced by transient-transfection in CHO cells and purification by immobilized protein A. The CDRs for these mAbs are disclosed in FIG. 5A of U.S. Pat. No. 8,273,354 and single chain Fv sequences are included in those employed in recombinant production as SEQ ID NOs: 9 and 10 respectively.

However, Fab 3D3 was generated from recombinantly produced 3D3 by incubation with immobilized papain, followed by removal of the Fc fragment with immobilized protein A. Fab 3D3 was then purified by Superdex 200 size-exclusion chromatography in 10 mM Tris-HCl pH 8.0 and 150 mM NaCl.

For recombinant scFv 2D10, included in SEQ ID NO:10, a synthetic gene codon-optimized for *Drosophila melanogaster* encoding 2D10 heavy chain variable region, a (GGGGS)3GGG linker, and 2D10 light chain variable region, was cloned into pMT-puro in-frame with an N-terminal BiP signal sequence and a C-terminal thrombin cleavage site followed by a Twin-Strep purification tag. The resulting scFv 2D10 expression plasmid was used to obtain stably-transfected Schneider 2 (S2) insect cells. Secreted scFv 2D10 was affinity purified on a StrepTrap column, digested with thrombin protease to remove the purification tag, and then purified by Superdex 200 size-exclusion chromatography in 10 mM Tris-HCl pH 8.0 and 150 mM NaCl.

B. Production of Epitopes

A synthetic gene encoding RSV G ectodomain (G[ecto]) P03423) was cloned into pCF in-frame with an N-terminal TPA signal sequence and C-terminal tandem 6-histidine and Twin-Strep purification tags (SEQ ID NO:7 that includes residues 64 to 298, UniProtKB entry). G[ecto] was produced by transient-transfection in CHO cells and secreted G[ecto] was affinity purified on a StrepTrap column.

A synthetic gene codon-optimized for *Escherichia coli* encoding RSV G residues 161 to 197 (G [161-197]) (SEQ ID NO:1 UniProtKB entry P03423) with a C-terminal 6-histidine purification tag (SEQ ID NO:8) was cloned into pET52b. The peptide was expressed overnight in *E. coli* BL21(DE3) at 18° C. The cells were then were lysed by ultrasonication in 20 mM Tris-HCl pH 8.0, 150 mM NaCl, and 25 mM imidazole (Buffer A) containing 2 µM $MgCl_2$, benzonase, and protease inhibitors. RSV G[161-197] was purified from soluble lysates by HisTrap FF affinity chromatography and eluted with a gradient into Buffer B (Buffer A containing 500 mM imidazole). Analogous methods were used to produce related peptides (G [162-172] (SEQ ID NO: 2) and G [169-198] (SEQ ID NO: 3)).

Example 2: ELISA Assays

Purified mAbs at a concentration of 5 pg/mL (150 µL total) were incubated overnight at room temperature in 96-well ELISA microtiter plates. Plates were then washed three times with PBS containing 0.05% TWEEN (polysorbate 20). Wells were blocked by adding 150 µL of 5% BSA in PBS and incubating at room temperature for 1 hr followed by three PBST washes. Recombinant RSV G[ecto] at 5 pg/mL or RSV G[161-197] at 20 pg/mL in 1% BSA in PBS was serially diluted 1:3 with 1% BSA in PBS. Wells were incubated with 150 µL RSV G protein for 1 hr at room temperature and the plates were washed three times with PBST. The plates were then incubated for 1 hr at room temperature with 150 µL HRP-conjugated-HisProbe (ThermoFisher Scientific) diluted 1:5000 in 1% BSA in PBS. Plates were washed three times with PBST and developed by adding peroxidase substrate o-phenylenediamine dihydrochloride (OPD) in 0.05 M phosphate-citrate buffer pH 5.0 and 1.5% hydrogen peroxide for 10 min at room temperature. The reactions were stopped by incubation with 2N sulfuric acid for 10 min at room temperature, and the absorbance was measured at 490 nm. ELISA experiments were performed in biological triplicates.

Example 3: Tests for Immunogenicity

The peptides, mutants and peptidomimetics of the invention are evaluated in a murine model using the following criteria.

TABLE 1

Immunogenicity Evaluation Criteria

| Category | Score | Detailed Criteria |
|---|---|---|
| RSV titers in lungs: Based on pfu/g lung tissue at day 5 post-challenge and RT-PCR quantitation of viral genomes/g tissue | 4 | no detectable RSV |
| | 3 | 75% reduction of RSV in lungs vs. naïve mice |
| | 2 | 50% reduction of RSV in lungs vs. naïve mice |
| | 1 | 25% reduction of RSV in lungs vs. naïve mice |
| Lung Pathology: Based on the mean score for each parameter, i.e. peribronchiolar, perivascular, interstitial and alveolar that involve each lung section evaluated | 4 | No pathology |
| | 3 | slight |
| | 2 | moderate |
| | 1 | severe |
| Duration of immunity: Based on full protection from subsequent virus challenge | 3 | >6 months |
| | 2 | 1-6 months |
| | 1 | <1 month |
| Weight loss: Parameter of morbidity | 3 | No weight loss |
| | 2 | 5-19% weight loss |
| | 1 | ≥20% weight loss |
| Cellular immunity: Th1/Th2 assayed by IFNγ and IL-4 ELISPOTs or by intracellular cytokine FACS and by ELISA of bronchial alveolar lavage fluid from the lungs | 3 | robust; Th1/Th2 balanced |
| | 2 | moderate; Th1/Th2 balanced |
| | 1 | Unbalanced Th2/Th1 |

Example 4: Chemotaxis Assay

An in vitro assay for RSV G modulation of CX3CR1 measures receptor mediated chemotaxis of human monocyte THP-1 cells {Tripp, R. A. et al. *Nature Immunology* (2001) 2:732-738}. In this assay, recombinant RSV G[161-197] induced chemotaxis at levels equivalent to the entire RSV G ectodomain, an activity blocked by pre-incubation with 3D3 or 2D10 or 3G12 at a level comparable to that provided by anti-CX3CR1 polyclonal serum. Table 2 provides the results of this analysis with respect to 3D3 and 2D10.

TABLE 2

Chemotaxis Assay Results

| Negative Control (serum free media) | Positive Control (+10% FBS) | RSV G[ecto] | RSV G[161-197] | RSV G[161-197] + 3D3 | RSV G[161-197] + 2D10 | RSV G[161-197] + anti-CX3CR1 |
|---|---|---|---|---|---|---|
| 1.0 | 5.2 | 3.9 | 4.2 | 1.5 | 1.0 | 1.1 |

In more detail, the assay was performed using a transwell insert plate with an 8 m pore size. Approximately 2 million log-phase THP-1 cells (a human leukemia monocytic cell line) washed twice and suspended in serum-free RPMI 1640 media were added to the upper chamber of the insert plate. Negative control was serum-free media alone to which serum-free media containing 25 nM mAb was added to the lower chamber. As a positive control, media containing 10% FBS was added to the lower chamber. RSV G[ecto] or RSV G[161-197] samples were added to the lower chamber at a final concentration of 5 nM in serum-free media. For samples with RSV G[161-197] and mAbs, RSV G[161-197] was pre-incubated with 5-molar excess mAb for 20 min at room temperature, and then added to serum-free media in the lower chamber, for a final concentration of 5 nM RSV G[161-197] and 25 nM mAb. For samples with anti-CX3CR1 antibody, 2 µL 1 mg/mL anti-CX3CR1 rabbit polyclonal antibody (ThermoFisher Scientific Cat #PA5-19910) was incubated with THP-1 cells for 30 minutes in the upper chamber before being placed into the well. The assembled plates were incubated in a CO2 incubator at 37° C. for 5 h. Cells migrated to the lower chamber were counted, and the chemotactic indices were determined by comparing the fold-increase in cell migration toward the chemoattractant to cell migration toward serum-free media alone. Experiments were performed in at least four biological replicates.

Example 5: Determination of Antibody-Epitope Interfaces by Crystallography

Formation and structure determination of the Fab 3D3-RSV G[162-172] complex. The synthetic peptide of Example 1B encoding RSV G amino acids 162 to 172 (UniProtKB entry P03423) (SEQ ID NO:2) was mixed in 5-molar excess with purified Fab 3D3 of Example 1A at 17.5 mg/ml in 10 mM Tris-HCl pH 8.0 and 150 mM NaCl. Crystals were grown by hanging drop vapor diffusion at 4° C. with a well solution of 23% PEG 3350 and 0.05 M zinc acetate. Crystals were transferred into a cryoprotectant solution of 26% PEG 3350, 0.05 M zinc acetate, and 25% ethylene glycol and flash frozen in liquid nitrogen. Diffraction data were collected at cryogenic temperature at the Advanced Light Source on beamline 8.3.1 using a wavelength of 1.11503 Å. Diffraction data from a single crystal were processed with iMosfim and Aimless. The Fab 3D3-RSV G[162-172] complex structure was solved by molecular replacement with a Fab homology model and the program PHASER, and the structure was refined and manually rebuilt using PHENIX and Coot, respectively. The final Fab 3D3-RSV G[162-172] complex structure (PDB code 5WNB) had the following Ramachandran statistics: 96.5% favored, 3.5% allowed, 0% outliers.

Formation and structure determination of the Fab 3D3-RSV G[161-197] complex. Purified RSV G[161-197] was mixed in 2 molar excess with purified Fab 3D3, dialyzed into 10 mM Tris-HCl pH 8.0 and 150 mM NaCl, and concentrated to 15 mg/mL. Crystals were grown by hanging drop vapor diffusion at 22° C. with a well solution of 21% PEG 3350 and 0.2 M ammonium citrate pH 7.0. Crystals were transferred into a cryoprotectant solution of 25% PEG 3350, 0.2 M ammonium citrate pH 7.0, and 25% glycerol and flash frozen in liquid nitrogen. Diffraction data were collected at cryogenic temperature at the Advanced Light Source beamline 8.3.1 using a wavelength of 1.11582 Å. Diffraction data were collected at cryogenic temperature at the Advanced Light Source on beamline 8.3.1 using a wavelength of 1.11503 Å. Diffraction data from a single crystal were processed with iMosfim and Aimless. The Fab 3D3-RSV G[161-197] complex structure was solved by molecular replacement with Fab 3D3 and the program PHASER, and the structure was refined and manually rebuilt using PHENIX and Coot, respectively. The final Fab 3D3-RSV G[161-197] complex structure (PDB code 5WNA) had the following Ramachandran statistics: 97.6% favored, 2.4% allowed, 0% outliers.

Formation and structure determination of the scFv 2D10-RSV G[169-198] complex. A synthetic peptide encoding RSV G amino acids 169 to 198 (SEQ ID NO: 3) (UniProtKB entry P03423) was mixed in 2-molar excess with purified scFv in 60 mM Tris-HCl pH 8.0 and 230 mM NaCl and concentrated to 15.0 mg/mL. Crystals were grown by hanging drop vapor diffusion at 22° C. with a well solution of 24% PEG 4000, 0.17 M ammonium sulfate, 0.085 M sodium citrate pH 5.6 and 15% glycerol. Crystals were transferred into a cryoprotectant solution of 28% PEG 4000, 0.17 M ammonium sulfate, 0.085 M sodium citrate pH 5.6 and 15% glycerol, and 25% glycerol and flash frozen in liquid nitrogen. Diffraction data were collected at cryogenic temperature at the Advanced Photon Source on beamline 23-ID-D using a wavelength of 1.033 Å. Diffraction data from a single crystal were processed with HKL2000. The scFv 2D10-RSV G[169-198] complex structure was solved by molecular replacement with a scFv homology model and the program PHASER, and the structure was refined and manually rebuilt using PHENIX and Coot, respectively. The final scFv 2D10-RSV G[169-198] complex structure (PDB code 5WN9) had the following Ramachandran statistics: 99.2% favored, 0.8% allowed, 0% outliers.

Formation and structure determination of the Fab 3G12-RSV G[157-197] complex. Purified RSV G[157-197] was mixed in 2 molar excess with purified Fab 3G12 and the complex was purified on a Superdex200 size-exclusion column in 10 mM Tris-HCl pH 8.0 and 150 mM NaCl. The complex was concentrated to 15.0 mg/mL. Crystals were grown by hanging drop vapor diffusion at 22° C. with a well solution of 1.8 M ammonium sulfate and 100 mM sodium acetate trihydrate pH 4.4. Crystals were transferred into a cryoprotectant solution of 2.0 M ammonium sulfate, 100 mM sodium acetate trihydrate pH 4.4, and 25% glycerol and flash frozen in liquid nitrogen. Diffraction data were collected at cryogenic temperature at the Advanced Light Source on beamline 8.3.1 using a wavelength of 1.11582 Å. Diffraction data from a single crystal were processed with iMosflm and Aimless. The Fab 3G12+RSV G[157-197] complex structure was solved by molecular replacement the program PHASER, and the structure was refined and manually rebuilt using PHENIX and Coot, respectively. The final Fab 3G12-RSV G[157-197] complex structure (PDB code 6MKC) had the following Ramachandran statistics: 95.7% favored, 4.3% allowed, 0% outliers.

Table 3 summarizes the crystallographic data (structures deposited in the Worldwide (PDB) Protein Data Bank).

change in size or shape resulting in a steric hinderance (steric clash) would be expected to result in a negative impact on such binding. Table 4 shows the results of representative substitutions in these residues in the RSV G CCR protein. Six representative mutants have been tested for their impact on CX3CR1 function as measured by the chemotaxis assay described in Example 4. Table 4 summarizes the results of duplicate assays (with standard deviations) using the standard one letter abbreviations for the amino acid at the indicated residue.

TABLE 3

Crystallographic data collection and refinement statistics[a]

| PDB code | 3D3-RSV G [162-172] 5WNB | 3D3-RSV G [161-197] 5WNA | 2D10-RSV G [169-198] 5WN9 | 3G12-RSV G [157-197] 6MKC |
|---|---|---|---|---|
| Data collection[b] | | | | |
| Space group | P 21 21 21 | P 1 21 1 | P 21 21 21 | P 31 2 1 |
| Cell dimensions | | | | |
| a, b, c (Å) | 68.76, 105.43, 121.82 | 64.62, 135.01, 73.78 | 44.84, 56.39, 126.15 | 139.33, 139.33, 94.7703 |
| α, β, γ (°) | 90.00, 90.00, 90.00 | 90.00, 107.45, 90.00 | 90.00, 90.00, 90.00 | 90.00, 90.00, 120.00 |
| Resolution (Å) | 48.38-2.40 (2.48-2.40) | 48.72-2.40 (2.48-2.40) | 50.00-1.55 (1.58-1.55) | 74.53-2.90 (3.08-2.90) |
| $R_{sym}$ or $R_{merge}$ | 0.122 (0.838) | 0.107 (0.763) | 0.058 (0.930) | 0.097 (0.641) |
| I/σI | 13.4 (3.1) | 12.3 (2.2) | 44.0 (1.4) | 9.4 (1.9) |
| Completeness (%) | 99.9 (99.8) | 99.5 (99.0) | 99.9 (99.4) | 99.5 (99.5) |
| Redundancy | 9.2 (8.3) | 6.3 (5.6) | 9.6 (6.2) | 3.9 (3.8) |
| $CC_{1/2}$ | 0.997 (0.808) | 0.996 (0.670) | 0.998 (0.751) | 0.993 (0.601) |
| Refinement | | | | |
| Resolution (Å) | 48.38-2.40 | 48.72-2.40 | 50.00-1.55 | 74.53-2.90 |
| No. reflections | 35,325 | 46,869 | 47,114 | 23,665 |
| $R_{work}/R_{free}$[c] | 0.218/0.280 | 0.192/0.246 | 0.169/0.185 | 0.193/0.209 |
| No. atoms | | | | |
| Protein | 6,586 | 7,124 | 3,810 | 3,595 |
| Ligand/ion | 22 | None | None | None |
| Water | 90 | 135 | 111 | None |
| B-factors | | | | |
| Protein | 50.29 | 42.02 | 34.04 | 66.24 |
| Ligand/ion | 63.66 | None | None | None |
| Water | 35.5 | 38.59 | 37.92 | None |
| R.m.s. deviations | | | | |
| Bond lengths (Å) | 0.005 | 0.006 | 0.008 | 0.019 |
| Bond angles (°) | 0.864 | 0.935 | 0.968 | 2.07 |

[a]For each structure, data from one crystal was used.
[b]Values in parentheses are for highest-resolution shell.
[c]$R_{free}$ was calculated using 5% of data excluded from refinement.

Example 6: Vaccines with Reduced Side Effects

Determination of structures of RSV G CCR protein in complex with the high affinity antibodies 2D10 and 3D3 shown in FIG. 4A-B provide a roadmap to design RSV G immunogens to disable CX3CR1 binding without disrupting the ability to generate high-affinity mAb epitopes. Specifically, six highly conserved amino acids have been identified whose side-chains make no molecular contacts with mAbs 3D3 and 2D10, so they can be substituted without impacting generation of high affinity mAbs similar to these mAbs. These residues are therefore candidates for substitution in order to interfere with binding to CX3CR1. Generally, providing an alteration in charge (charge switch) and/or a

TABLE 4

CX3CR1 DISRUPTING MUTATIONS.

| Mechanism of disabling activity | RSV G (CCR) variants | Chemotactic activity |
|---|---|---|
| | Negative control (PBS) | 1.0 |
| | Wild type RSV G (CCR) | 6.2 (0.7) |
| Steric clash | H164→Y | 3.8 (0.4) |
| Charge switch | E166→K | 1.6 (0.7) |
| Steric clash | S177→W | 1.2 (0.4) |
| Steric clash | S177→R | 0.9 (0.2) |

TABLE 4-continued

CX3CR1 DISRUPTING MUTATIONS.

| Mechanism of disabling activity | RSV G (CCR) variants | Chemotactic activity |
|---|---|---|
| Charge switch | E166→K + K187 →E | 1.8 (0.1) |
| Charge switch | K192→E + K193 →E | 2.5 (0.7) |

As shown, each of these mutations shows diminished chemotactic activity, the most effective being the substitution of arginine for serine at position 177. Combinations of these mutations are included within the scope of the invention.

Example 7: Stabilization of Epitope Mimics

Chemically synthesized peptide technology, aided by combinatorial chemistry methods for synthesis and assay, now constitutes a mature technology for creating epitope mimics, with new advances enabling construction and screening of very large libraries (billions of compounds) by using DNA tags and next generation sequencing to deconvolute the hits {Chan, A. I., et al. *Curr Opin Chem Biol.* (2015) 26: 55-61}. For example, helical conformations can be stabilized through the insertion of amino acids with restricted conformational space, such as alpha-methylated amino acids (e.g. Aib), by side-chain cross-linking or 'stapling' to stabilize helical epitopes, and by the use of helix caps and hydrogen-bond surrogates. Examples include hydrazone crosslinks as hydrogen bond surrogates, Freidinger-like lactams and pseudoprolines to stabilize turns {Estieu-Gionnet, K. and Guichard, G. Exp. Opin. Drug Discov. (2011) 6: 937-963}.

Further, techniques known in the art for in vitro translation of mRNA into protein allow introduction of non-standard amino acids into proteins and peptides, facilitating formation of crosslinked peptides {Hartman, M. C., et al. *PLoS One* (2007) 2(10):e972}.

Example 8: Identification of Non-Immunoglobulin Binding Agents

The peptides, mutants and peptidomimetics of the invention can be used to identify effective non-immunoglobulin binding agents.

A variety of non-immunoglobulin protein scaffolds is known in the art that provide equivalent pharmacological activity arising from high affinity, high specificity binding to an epitope similar to one bound by a traditional mAb {Sha, F, et al. *Protein Sci.* (2017) 26(5):910-924}. Examples include scaffolds based on fibronectin, lipocalin, lens crystallin, tetranectin, ankyrin, Protein A (Ig binding domain). Small peptide families may also have antibody-like affinity and specificity, including avian pancreatic peptides and conotoxins {Josephson, K., et al., *J. Am. Chem. Soc.*(2005) 127:11727-11725}. Cross-linked peptides similarly provide the ability to generate high affinity binding agents with well-defined specificity. In addition, non-protein based agents such as nucleic acid aptamers can also provide equivalent binding {Sun, H. and Zu, Y. Molecules (2015) 20(7):11959-80}.

Summary of Disclosed Sequences

In the table below, for the listed sequences that state that they include "plus additions" are those wherein the coding sequence of interest is supplemented by aids to expression and/or purification, such as a start codon, a glycine spacer, a histidine tag, or other purification aid such as Twin-Strep {Schmidt, T. G., et al. *Protein Expr Purif* (2013) 92(1):54-61}. These are provided in more detail in the sequence listing that follows.

| SEQ ID NO | Composition (amino acid and encoding nucleic acid) |
|---|---|
| 1 | Residues 161-197 of RSVG |
| 2 | Residues 162-172 of RSVG |
| 3 | Residues 169-198 of RSVG |
| 4 | Residues 157-197 of RSVG |
| 5 | Residues 148-197 of RSVG |
| 6 | Residues 161-195 of RSVG |
| 7 | Residues 64-298 of RSVG plus additions |
| 8 | Residues 161-197 of RSVG plus additions |
| 9 | Residues 157-197 of RSVG plus additions |
| 10 | Residues 148-197 of RSVG plus additions |
| 11 | Residues 161-195 of RSVG plus additions |
| 12 | mAb 303 single chain Fv plus additions |
| 13 | mAb 2D10 single chain Fv plus additions |

Sequence Listings
SEQ ID NO 1
LENGTH: 37 amino acids
TYPE: PRT
ORGANISM: Artificial Sequence
FEATURE: Immunogen recognized by mAbs 3D3, 2D10 and 3G12
OTHER INFORMATION: RSV G protein [residues 161-197]
SEQUENCE

NDFHFEVFNFVPCSICSNNPTCWAICKRIPNKKPGKK

SEQ ID NO 2
LENGTH: 11 amino acids
TYPE: PRT
ORGANISM: Artificial Sequence
FEATURE: Immunogen recognized by mAb 3D3 but not mAb 2D10
OTHER INFORMATION: RSV G protein [residues 162-172]
SEQUENCE

DFHFEVFNFVP

SEQ ID NO 3
LENGTH: 30 amino acids
TYPE: PRT
ORGANISM: Artificial Sequence
FEATURE: Immunogen recognized by mAb 2D10 but not mAb 3D3
OTHER INFORMATION: RSV G protein [residues 169-198]
SEQUENCE

NFVPCSICSNNPTCWAICKRIPNKKPGKKT

SEQ ID NO 4
LENGTH: 50 amino acids
TYPE: PRT
ORGANISM: Artificial Sequence
FEATURE: Immunogen recognized by mAbs 3D3, 2D10, and 3G12
OTHER INFORMATION: RSV G protein [residues 157-197]

SKPNNDFHFEVFNFVPCSICSNNPTCWAICKRIPNKKPGKK

SEQ ID NO 5
LENGTH: 45 amino acids
TYPE: PRT
ORGANISM: Artificial Sequence
FEATURE: Immunogen recognized by mAbs
OTHER INFORMATION: RSV G protein [residues 148-197]
SEQUENCE

TKQRQNKPPSKPNNDFHFEVFNFVPCSICSNNPTCWAICKRIPNKKPGKK

SEQ ID NO 6
LENGTH: 31 amino acids
TYPE: PRT
ORGANISM: Artificial Sequence
FEATURE: Immunogen recognized by mAbs
OTHER INFORMATION: RSV G protein [residues 161-191]
SEQUENCE

NDFHFEVFNFVPCSICSNNPTCWAICKRIPN

SEQ ID NO 7
LENGTH: 295 amino acids
TYPE: PRT
ORGANISM: Artificial Sequence
FEATURE: Immunogen
OTHER INFORMATION: RSV G protein ectodomain [residues 64-298 from RSV strain A2, GenBank KT992094.1, with 2 synonymous mutatations (underlined)] with N terminal TPA secretion signal and C terminal 6His-2Strep tag
SEQUENCE

MDAMKRGLCCVLLLCGAVFVSPSEFSANHKVTPTTAIIQDATSQIKNTTP

TYLTQNPQLGISPSNPSEITSQITTILASTTPGVKSTLQSTTVKTKNTTT

TQTQPSKPTTKQRQNKPPSKPNNDFHFEVFNFVPCSICSNNPTCWAICKR

IPNKKPGKKTTTKPTKKPTLKTTKKDPKPQTTKSKEVPTTKPTEEPTINT

TKTNIITTLLTSNTTGNPELTSQMETFHSTSSEGNPSPSQVSTTSEYPSQ

PSSPPNTPRQHHHHHHGWSHPQFEKGGGSGGGSGGGSWSHPQFEK

SEQ ID NO 14
DNA sequence:

ATGGACGCCATGAAGCGGGGCCTGTGCTGTGTGCTGCTGCTGTGCGGAGC

CGTGTTCGTGTCCCCCAGCGAATTCTCGGCAAACCACAAAGTCACACCAA

CAACTGCAATCATACAAGATGCAACAAGCCAGATCAAGAACACAACCCCA

ACATACCTCACCCAGAATCCTCAGCTTGGAATCAGTCCCTCTAATCCGTC

TGAAATTACATCACAAATCACCACCATACTAGCTTCAACAACACCAGGAG

TCAAGTCAACCCTGCAATCCACAACAGTCAAGACCAAGAACACAACGACA

ACTCAAACACAACCCAGCAAGCCCACCACAAAACAACGCCAAACAAACC

ACCAAGCAAACCCAATAATGATTTTCACTTTGAAGTGTTCAACTTTGTAC

CCTGCAGCATATGCAGCAACAATCCAACCTGCTGGGCTATCTGCAAAAGA

ATACCAAACAAAAAACCAGGAAAGAAAACCACTACCAAGCCCACAAAAAA

ACCAACCCTCAAGACAACCAAAAAAGATCCCAAACCTCAAACCACTAAAT

CAAAGGAAGTACCCACCACCAAGCCCACAGAAGAGCCAACCATCAACACC

ACCAAAACAAACATCATAACTACACTACTCACCTCCAACACCACAGGAAA

TCCAGAACTCACAAGTCAAATGGAAACCTTCCACTCAACTTCCTCCGAAG

GCAATCCAAGCCCTTCTCAAGTCTCTACAACATCCGAGTACCCATCACAA

CCTTCATCTCCACCCAACACT<u>C</u>CT<u>C</u>GCCAGCACCATCACCACCATCATGG

*TTGGAGTCATCCACAATTCGAGAAGGGCGGCGGCTCCGGAGGTGGATCAG*

*GAGGTGGTTCCTGGTCACACCCTCAATTCGAGAAGTGA*

SEQ ID NO 8
LENGTH: 45 amino acids
TYPE: PRT
ORGANISM: Artificial Sequence
FEATURE: Contains Immunogen
OTHER INFORMATION: RSV G protein [residues 161-197] with N terminal start codon and spacer glycine and C terminal 6His tag
SEQUENCE

M*G*NDFHFEVFNFVPCSICSNNPTCWAICKRIPNKKPGKK*HHHHHH*

SEQ ID NO 15
DNA sequence:

*ATGGGAAACGACTTCCACTTCGAGGTGTTCAACTTCGTTCCGTGCAGCAT*

*TTGCAGCAACAACCCGACCTGCTGGGCGATCTGCAAACGTATCCCGAACA*

*AGAAACCGGGTAAGAAACATCACCATCACCATCACTGA*

SEQ ID NO 9
LENGTH: 54 amino acids
TYPE: PRT
ORGANISM: Artificial Sequence
FEATURE: Contains Immunogen
OTHER INFORMATION: RSV G protein [residues 157-197] with N terminal start codon and spacer glycine and C terminal 6His tag
SEQUENCE

M*G*SKPNNDFHFEVFNFVPCSICSNNPTCWAICKRIPNKKPGKK*HHHHHH*

SEQ ID NO 16
DNA sequence:

*ATGGGAAGCAAACCGAACAACGACTTCCACTTCGAGGTGTTCAACTTCGT*

*TCCGTGCAGCATTTGCAGCAACAACCCGACCTGCTGGGCGATCTGCAAAC*

*GTATCCCGAACAAGAAACCGGGTAAGAAACATCACCATCACCATCACTGA*

SEQ ID NO 10
LENGTH: 45 amino acids
TYPE: PRT
ORGANISM: Artificial Sequence
FEATURE: Contains Immunogen
OTHER INFORMATION: RSV G protein [residues 148-197] with N terminal start codon and spacer glycine and C terminal 6His tag

SEQUENCE

*MGTKQRQNKSKPNNDFHFEVFNFVPCSICSNNPTCWAICKRIPNKKPGKK*

*HHHHHH*

SEQ ID NO 17
DNA sequence:

*ATGGGAACCAAGCAGCGTCAGAACAAGCCGCCGAGCAAACCGAACAACGA*

*CTTCCACTTCGAGGTGTTCAACTTCGTTCCGTGCAGCATTTGCAGCAACA*

*ACCCGACCTGCTGGGCGATCTGCAAACGTATCCCGAACAAGAAACCGGGT*

*AAGAAACATCACCATCACCATCACTGA*

SEQ ID NO 11
LENGTH: 39 amino acids
TYPE: PRT
ORGANISM: Artificial Sequence
FEATURE: Immunogen
OTHER INFORMATION: RSV G protein [residues 161-195] with N terminal start codon and spacer glycine and C terminal 6His tag
SEQUENCE

*MGNDFHFEVFNFVPCSICSNNPTCWAICKRIPNHHHHHH*

SEQ ID NO 18
DNA sequence:

*ATGGGAAACGACTTCCACTTCGAGGTGTTCAACTTCGTTCCGTGCAGCAT*

*TTGCAGCAACAACCCGACCTGCTGGGCGATCTGCAAACGTATCCCGAACA*

*AGAAACCGGGTCATCACCATCACCATCACTGA*

SEQ ID NO 12
LENGTH: 308 amino acids
TYPE: PRT
ORGANISM: Artificial Sequence
FEATURE: Single-chain antibody
OTHER INFORMATION: mAb 3D3 single chain Fv (scFv 3D3) with N terminal Bip signal sequence, internal flexible linker and C terminal thrombin protease cleavage site followed by 6His-2Strep tag
SEQUENCE

*MKLCILLAVVAFVGLSLGRS*EEQLVESGGGLVQPGRSLRLSCVGSGLRFE

EHAMHWVRQAPGRGLEWVSGISWNSGSVGYADSVKGRFTTSRDNAKDILF

LEMNTLRSEDTALYFCAIMVATTKNDFHYYKDVWGKGTTVTVSS*GGGGSG*

*GGGSGGGGS*QIVLTQSPATLSLSPGERATLSCRASQSVSNHLAWYQQKPG

QAPRLLIYETSNRATGIPPRFSGSGSGTDFTLTISSLEPEDFAVYYCQQR

NNWYTFGQGTKLEIKA*SLVPRGSGWSHPQFEKGGGSGGGSGGGSWSHPQF*

*EK*

SEQ ID NO 19
DNA sequence:

*ATGAAGTTATGCATATTACTGGCCGTCGTGGCCTTTGTTGGCCTCTCGCT*

*CGGGAGATCTG*AAGAGCAACTGGTGGAGAGCGGTGGTGGTCTGGTTCAGC

CGGGTCGTTCCCTGCGTCTGTCCTGCGTGGGTAGCGGTCTGCGTTTTGAG

GAGCACGCGATGCACTGGGTGCGTCAGGCACCGGGTCGCGGTCTGGAGTG

GGTGAGCGGTATCAGCTGGAACAGCGGTAGCGTGGGTTATGCCGACAGCG

TGAAGGGCCGTTTCACCACCAGCCGCGACAACGCCAAGGATATCCTGTTC

CTGGAGATGAACACCCTGCGTAGCGAGGATACCGCGCTGTACTTCTGCGC

GATTATGGTGGCCACCACCAAGAACGACTTCCACTACTACAAGGATGTGT

GGGGCAAGGGCACCACCGTGACCGTGAGCAGT*GGCGGCGGTGGCAGCGGC*

*GGTGGCGGTAGCGGTGGCGGTGGCAGC*CAGATTGTGCTGACCCAGAGCCC

GGCAACCCTGAGCCTGAGCCCGGGCGAGCGTGCCACCCTGAGCTGCCGTG

CAAGCCAGAGCGTGAGCAACCACCTGGCGTGGTATCAGCAGAAGCCGGGT

CAGGCGCCGCGTCTGCTGATCTACGAAACCAGCAACCGTGCCACCGGCAT

TCCGCCGCGCTTCAGCGGCAGCGGTAGCGGCACCGACTTCACCCTGACCA

TTAGCAGCCTGGAGCCGGAGGATTTCGCCGTGTACTATTGCCAACAGCGT

AACAACTGGTACACCTTCGGTCAGGGCACCAAACTGGAAATCAAAGCTAG

*CCTGGTTCCCCGCGGATCGGGTTGGAGTCATCCACAATTCGAGAAGGGCG*

*GCGGCTCCGGAGGTGGATCAGGAGGTGGTTCCTGGTCACACCCTCAATTC*

*GAGAAGTGA*

SEQ ID NO 13
LENGTH: 315 amino acids
TYPE: PRT
ORGANISM: Artificial Sequence
FEATURE: Single-chain antibody
OTHER INFORMATION: mAb 2D10 single chain Fv (scFv 2D10) with N terminal Bip signal sequence, internal flexible linker and C terminal thrombin protease cleavage site followed by 6His-2Strep tag
SEQUENCE

*MKLCILLAVVAFVGLSLGRS*QVQLVQSGPEVKKPGASVRLSCKASGYVFT

NYGVSWVRQAPGQGLEWMGWSSPYNGNTYYAQKLKARVTMTTDTSTNTAY

MELRSLRSDDTAVYYCGRDMLGVVQAVAGPFDSWGQGTLVTVSSAS*GGGG*

*SGGGGSGGGGSGGG*DTPMTQSPSSVSASVGDRVTISCRASQGISNSLAWY

QQKLGKAPQLLIYAASSLQSGVPSRFSGSGSGTDFTLTISSLQPEDFATY

YCQQTNTFPFTFGPGTKVEVRRA*SLVPRGSGWSHPQFEKGGGSGGGSGGG*

*SWSHPQFEK*

SEQ ID NO 20
DNA sequence:

*ATGAAGTTATGCATATTACTGGCCGTCGTGGCCTTTGTTGGCCTCTCGCT*

*CGGGAGATCT*CAGGTGCAGCTGGTGCAGAGCGGCCCCGGAAGTGAAAAGC

CGGGCGCAAGCGTGCGTCTGTCTTGCAAAGCATCCGGTTACGTGTTCACC

AACTACGGTGTGAGCTGGGTGCGCCAGGCTCCTGGTCAGGGCCTGGAATG

GATGGGTTGGAGCAGCCCATACAACGGTAACACCTACTATGCGCAGAAAC

TGAAGGCTCGTGTGACCATGACCACCGACACCAGCACCAACACCGCATAC

ATGGAGCTGCGTAGCCTGCGCTCTGACGATACCGCCGTGTATTACTGCGG
TCGCGATATGCTGGGTGTGGTGCAGGCAGTGGCGGGTCCATTCGACTCCT
GGGGTCAGGGCACCCTGGTGACCGTGTCCTCTGCAAGC*GGCGGTGGTGGT*
*TCTGGTGGCGGCGGTAGCGGTGGTGGCGGTAGCGGCGGCGGTGACACCCC*
AATGACCCAGTCTCCGTCCTCTGTGTCTGCTTCCGTGGGCGATCGCGTGA
CCATCTCCTGCCGCGCATCTCAGGGCATTAGCAACTCTCTGGCATGGTAT
CAGCAGAAACTGGGCAAGGCTCCACAGCTGCTGATCTATGCGGCATCCTC

TCTGCAGAGCGGTGTGCCTTCTCGTTTCTCCGGTAGCGGCTCCGGCACCG
ATTTCACCCTGACCATCTCCAGCCTGCAGCCAGAGGATTTCGCTACCTAC
TATTGCCAGCAGACCAACACCTTCCCATTCACCTTCGGCCCTGGCACCAA
AGTGGAAGTGCGTCGC*GCTAGCCTGGTTCCCCGCGGATCGGGTTGGAGTC*
*ATCCACAATTCGAGAAGGGCGGCGGCTCCGGAGGTGGATCAGGAGGTGGT*
*TCCTGGTCACACCCTCAATTCGAGAAGTGA*

---

The invention claimed is:

1. A mutant peptide or peptidomimetic thereof, the mutant peptide or peptidomimetic comprising:
   (a) amino acid residues 161-197 of respiratory syncytial virus (RSV) G protein, as set forth as SEQ ID NO: 1, with at least one amino acid substitution at amino acid residue 162, 164, 166, 177, 187, 192, or 193 thereof;
   (b) amino acid residues 162-172 of RSV G protein, as set forth as SEQ ID NO: 2, with at least one amino acid substitution at amino acid residue 162, 164, or 166 thereof;
   (c) amino acid residues 169-198 of RSV G protein, as set forth as SEQ ID NO: 3, with at least one amino acid substitution at amino acid residue 177, 187, 192, or 193 thereof;
   (d) amino acid residues 157-197 of RSV G protein, as set forth as SEQ ID NO: 4, with at least one amino acid substitution at amino acid residue 162, 164, 166, 177, 187, 192, or 193 thereof;
   (e) amino acid residues 148-197 of RSV G protein, as set forth as SEQ ID NO: 5, with at least one amino acid substitution at amino acid residue 162, 164, 166, 177, 187, 192, or 193 thereof; or
   (f) amino acid residues 161-191 of RSV G protein, as set forth as SEQ ID NO: 6, with at least one amino acid substitution at amino acid residue 162, 164, 166, 177, or 187 thereof;

wherein the mutant peptide or peptidomimetic (i) comprises diminished activation of CX3CR1 (chemokine receptor responsive to fractalkine) as compared to the respective unmodified peptide comprising SEQ ID NOS: 1-6, (ii) is immunoreactive with mAb 3D3, and/or 2D10 and/or 3G12, and (iii) is chemically stabilized to maintain its native conformation when binding to mAb 3D3, and/or 2D10 and/or 3G12.

2. The mutant or peptidomimetic of claim 1 which elicits sub-nM affinity antibodies immunoreactive with an epitope of RSV G protein conserved between A and B strains of the virus.

3. The mutant or peptidomimetic of claim 1, wherein the substituted amino acid of (a)-(f) comprises a different charge than the unsubstituted amino acid.

4. The mutant or peptidomimetic of claim 1, wherein the substituted amino acid of (a)-(f) comprises a different size or shape than the unsubstituted amino acid.

5. The mutant or peptidomimetic of claim 1, wherein the substituted amino acid of (a)-(f) comprises a different side chain than the unsubstituted amino acid.

6. The mutant or peptidomimetic of claim 1, wherein the at least one substitution provided in (a)-(f) comprises a tyrosine for histidine at amino acid position 164, a lysine for glutamate at amino acid position 166, a tryptophan for serine at amino acid position 177, or arginine for serine at amino acid position 177, or combination thereof.

7. The mutant or peptidomimetic of claim 1, wherein the at least one substitution provided in (a)-(f) comprises a lysine for glutamate at amino acid position 166 and glutamate for lysine at amino acid position 187.

8. The mutant or peptidomimetic of claim 1, wherein the at least one substitution provided in (a) and (c) comprises a glutamate for lysine at amino acid positions 192 and 193.

9. A pharmaceutical or veterinary composition or vaccine that comprises as active agent the mutant or peptidomimetic of claim 1.

* * * * *

SEQUENCE LISTING

<160> NUMBER OF SEQ ID NOS: 20

<210> SEQ ID NO 1
<211> LENGTH: 37
<212> TYPE: PRT
<213> ORGANISM: Artificial Sequence
<220> FEATURE:
<223> OTHER INFORMATION: Synthetic Construct

<400> SEQUENCE: 1

Asn Asp Phe His Phe Glu Val Phe Asn Phe Val Pro Cys Ser Ile Cys
1               5                   10                  15

Ser Asn Asn Pro Thr Cys Trp Ala Ile Cys Lys Arg Ile Pro Asn Lys
            20                  25                  30

Lys Pro Gly Lys Lys
        35

<210> SEQ ID NO 2
<211> LENGTH: 11
<212> TYPE: PRT
<213> ORGANISM: Artificial Sequence
<220> FEATURE:
<223> OTHER INFORMATION: Synthetic Construct

<400> SEQUENCE: 2

Asp Phe His Phe Glu Val Phe Asn Phe Val Pro
1               5                   10

<210> SEQ ID NO 3
<211> LENGTH: 30
<212> TYPE: PRT
<213> ORGANISM: Artificial Sequence
<220> FEATURE:
<223> OTHER INFORMATION: Synthetic Construct

<400> SEQUENCE: 3

Asn Phe Val Pro Cys Ser Ile Cys Ser Asn Asn Pro Thr Cys Trp Ala
1               5                   10                  15

Ile Cys Lys Arg Ile Pro Asn Lys Lys Pro Gly Lys Lys Thr
            20                  25                  30

<210> SEQ ID NO 4
<211> LENGTH: 41
<212> TYPE: PRT
<213> ORGANISM: Artificial Sequence
<220> FEATURE:
<223> OTHER INFORMATION: Synthetic Construct

<400> SEQUENCE: 4

Ser Lys Pro Asn Asn Asp Phe His Phe Glu Val Phe Asn Phe Val Pro
1               5                   10                  15

```
Cys Ser Ile Cys Ser Asn Asn Pro Thr Cys Trp Ala Ile Cys Lys Arg
            20                  25                  30

Ile Pro Asn Lys Lys Pro Gly Lys Lys
            35                  40

<210> SEQ ID NO 5
<211> LENGTH: 50
<212> TYPE: PRT
<213> ORGANISM: Artificial Sequence
<220> FEATURE:
<223> OTHER INFORMATION: Synthetic Construct

<400> SEQUENCE: 5

Thr Lys Gln Arg Gln Asn Lys Pro Pro Ser Lys Pro Asn Asn Asp Phe
1               5                   10                  15

His Phe Glu Val Phe Asn Phe Val Pro Cys Ser Ile Cys Ser Asn Asn
            20                  25                  30

Pro Thr Cys Trp Ala Ile Cys Lys Arg Ile Pro Asn Lys Lys Pro Gly
            35                  40                  45

Lys Lys
    50

<210> SEQ ID NO 6
<211> LENGTH: 31
<212> TYPE: PRT
<213> ORGANISM: Artificial Sequence
<220> FEATURE:
<223> OTHER INFORMATION: Synthetic Construct

<400> SEQUENCE: 6

Asn Asp Phe His Phe Glu Val Phe Asn Phe Val Pro Cys Ser Ile Cys
1               5                   10                  15

Ser Asn Asn Pro Thr Cys Trp Ala Ile Cys Lys Arg Ile Pro Asn
            20                  25                  30

<210> SEQ ID NO 7
<211> LENGTH: 295
<212> TYPE: PRT
<213> ORGANISM: Artificial Sequence
<220> FEATURE:
<223> OTHER INFORMATION: Synthetic Construct

<400> SEQUENCE: 7

Met Asp Ala Met Lys Arg Gly Leu Cys Cys Val Leu Leu Leu Cys Gly
1               5                   10                  15

Ala Val Phe Val Ser Pro Ser Glu Phe Ser Ala Asn His Lys Val Thr
            20                  25                  30

Pro Thr Thr Ala Ile Ile Gln Asp Ala Thr Ser Gln Ile Lys Asn Thr
            35                  40                  45

Thr Pro Thr Tyr Leu Thr Gln Asn Pro Gln Leu Gly Ile Ser Pro Ser
        50                  55                  60

Asn Pro Ser Glu Ile Thr Ser Gln Ile Thr Thr Ile Leu Ala Ser Thr
65              70                  75                  80

Thr Pro Gly Val Lys Ser Thr Leu Gln Ser Thr Thr Val Lys Thr Lys
            85                  90                  95

Asn Thr Thr Thr Thr Gln Thr Gln Pro Ser Lys Pro Thr Thr Lys Gln
            100                 105                 110

Arg Gln Asn Lys Pro Pro Ser Lys Pro Asn Asn Asp Phe His Phe Glu
        115                 120                 125
```

```
Val Phe Asn Phe Val Pro Cys Ser Ile Cys Ser Asn Asn Pro Thr Cys
            130                 135                 140

Trp Ala Ile Cys Lys Arg Ile Pro Asn Lys Lys Pro Gly Lys Lys Thr
145                 150                 155                 160

Thr Thr Lys Pro Thr Lys Lys Pro Thr Leu Lys Thr Thr Lys Lys Asp
                165                 170                 175

Pro Lys Pro Gln Thr Thr Lys Ser Lys Glu Val Pro Thr Thr Lys Pro
                180                 185                 190

Thr Glu Glu Pro Thr Ile Asn Thr Thr Lys Thr Asn Ile Ile Thr Thr
                195                 200                 205

Leu Leu Thr Ser Asn Thr Thr Gly Asn Pro Glu Leu Thr Ser Gln Met
210                 215                 220

Glu Thr Phe His Ser Thr Ser Ser Glu Gly Asn Pro Ser Pro Ser Gln
225                 230                 235                 240

Val Ser Thr Thr Ser Glu Tyr Pro Ser Gln Pro Ser Ser Pro Pro Asn
                245                 250                 255

Thr Pro Arg Gln His His His His His His Gly Trp Ser His Pro Gln
                260                 265                 270

Phe Glu Lys Gly Gly Gly Ser Gly Gly Gly Ser Gly Gly Gly Ser Trp
                275                 280                 285

Ser His Pro Gln Phe Glu Lys
290                 295

<210> SEQ ID NO 8
<211> LENGTH: 45
<212> TYPE: PRT
<213> ORGANISM: Artificial Sequence
<220> FEATURE:
<223> OTHER INFORMATION: Synthetic Construct

<400> SEQUENCE: 8

Met Gly Asn Asp Phe His Phe Glu Val Phe Asn Phe Val Pro Cys Ser
1               5                   10                  15

Ile Cys Ser Asn Asn Pro Thr Cys Trp Ala Ile Cys Lys Arg Ile Pro
                20                  25                  30

Asn Lys Lys Pro Gly Lys Lys His His His His His
                35                  40                  45

<210> SEQ ID NO 9
<211> LENGTH: 49
<212> TYPE: PRT
<213> ORGANISM: Artificial Sequence
<220> FEATURE:
<223> OTHER INFORMATION: Synthetic Construct

<400> SEQUENCE: 9

Met Gly Ser Lys Pro Asn Asn Asp Phe His Phe Glu Val Phe Asn Phe
1               5                   10                  15

Val Pro Cys Ser Ile Cys Ser Asn Asn Pro Thr Cys Trp Ala Ile Cys
                20                  25                  30

Lys Arg Ile Pro Asn Lys Lys Pro Gly Lys Lys His His His His
                35                  40                  45

His

<210> SEQ ID NO 10
<211> LENGTH: 56
<212> TYPE: PRT
<213> ORGANISM: Artificial Sequence
<220> FEATURE:
```

<223> OTHER INFORMATION: Synthetic Construct

<400> SEQUENCE: 10

Met Gly Thr Lys Gln Arg Gln Asn Lys Ser Lys Pro Asn Asn Asp Phe
1               5                   10                  15

His Phe Glu Val Phe Asn Phe Val Pro Cys Ser Ile Cys Ser Asn Asn
            20                  25                  30

Pro Thr Cys Trp Ala Ile Cys Lys Arg Ile Pro Asn Lys Lys Pro Gly
        35                  40                  45

Lys Lys His His His His His His
    50                  55

<210> SEQ ID NO 11
<211> LENGTH: 39
<212> TYPE: PRT
<213> ORGANISM: Artificial Sequence
<220> FEATURE:
<223> OTHER INFORMATION: Synthetic Construct

<400> SEQUENCE: 11

Met Gly Asn Asp Phe His Phe Glu Val Phe Asn Phe Val Pro Cys Ser
1               5                   10                  15

Ile Cys Ser Asn Asn Pro Thr Cys Trp Ala Ile Cys Lys Arg Ile Pro
            20                  25                  30

Asn His His His His His His
        35

<210> SEQ ID NO 12
<211> LENGTH: 302
<212> TYPE: PRT
<213> ORGANISM: Artificial Sequence
<220> FEATURE:
<223> OTHER INFORMATION: Synthetic Construct

<400> SEQUENCE: 12

Met Lys Leu Cys Ile Leu Leu Ala Val Val Ala Phe Val Gly Leu Ser
1               5                   10                  15

Leu Gly Arg Ser Glu Glu Gln Leu Val Glu Ser Gly Gly Gly Leu Val
            20                  25                  30

Gln Pro Gly Arg Ser Leu Arg Leu Ser Cys Val Gly Ser Gly Leu Arg
        35                  40                  45

Phe Glu Glu His Ala Met His Trp Val Arg Gln Ala Pro Gly Arg Gly
    50                  55                  60

Leu Glu Trp Val Ser Gly Ile Ser Trp Asn Ser Gly Ser Val Gly Tyr
65                  70                  75                  80

Ala Asp Ser Val Lys Gly Arg Phe Thr Thr Ser Arg Asp Asn Ala Lys
                85                  90                  95

Asp Ile Leu Phe Leu Glu Met Asn Thr Leu Arg Ser Glu Asp Thr Ala
            100                 105                 110

Leu Tyr Phe Cys Ala Ile Met Val Ala Thr Thr Lys Asn Asp Phe His
        115                 120                 125

Tyr Tyr Lys Asp Val Trp Gly Lys Gly Thr Thr Val Thr Val Ser Ser
    130                 135                 140

Gly Gly Gly Gly Ser Gly Gly Gly Gly Ser Gly Gly Gly Gly Ser Gln
145                 150                 155                 160

Ile Val Leu Thr Gln Ser Pro Ala Thr Leu Ser Leu Ser Pro Gly Glu
                165                 170                 175

Arg Ala Thr Leu Ser Cys Arg Ala Ser Gln Ser Val Ser Asn His Leu

```
                   180                 185                 190
Ala Trp Tyr Gln Gln Lys Pro Gly Gln Ala Pro Arg Leu Leu Ile Tyr
                195                 200                 205

Glu Thr Ser Asn Arg Ala Thr Gly Ile Pro Pro Arg Phe Ser Gly Ser
            210                 215                 220

Gly Ser Gly Thr Asp Phe Thr Leu Thr Ile Ser Ser Leu Glu Pro Glu
225                 230                 235                 240

Asp Phe Ala Val Tyr Tyr Cys Gln Gln Arg Asn Asn Trp Tyr Thr Phe
                245                 250                 255

Gly Gln Gly Thr Lys Leu Glu Ile Lys Ala Ser Leu Val Pro Arg Gly
                260                 265                 270

Ser Gly Trp Ser His Pro Gln Phe Glu Lys Gly Gly Ser Gly Gly
                275                 280                 285

Gly Ser Gly Gly Gly Ser Trp Ser His Pro Gln Phe Glu Lys
            290                 295                 300

<210> SEQ ID NO 13
<211> LENGTH: 309
<212> TYPE: PRT
<213> ORGANISM: Artificial Sequence
<220> FEATURE:
<223> OTHER INFORMATION: Synthetic Construct

<400> SEQUENCE: 13

Met Lys Leu Cys Ile Leu Leu Ala Val Val Ala Phe Val Gly Leu Ser
1               5                   10                  15

Leu Gly Arg Ser Gln Val Gln Leu Val Gln Ser Gly Pro Glu Val Lys
            20                  25                  30

Lys Pro Gly Ala Ser Val Arg Leu Ser Cys Lys Ala Ser Gly Tyr Val
        35                  40                  45

Phe Thr Asn Tyr Gly Val Ser Trp Val Arg Gln Ala Pro Gly Gln Gly
    50                  55                  60

Leu Glu Trp Met Gly Trp Ser Ser Pro Tyr Asn Gly Asn Thr Tyr Tyr
65                  70                  75                  80

Ala Gln Lys Leu Lys Ala Arg Val Thr Met Thr Thr Asp Thr Ser Thr
                85                  90                  95

Asn Thr Ala Tyr Met Glu Leu Arg Ser Leu Arg Ser Asp Asp Thr Ala
            100                 105                 110

Val Tyr Tyr Cys Gly Arg Asp Met Leu Gly Val Val Gln Ala Val Ala
        115                 120                 125

Gly Pro Phe Asp Ser Trp Gly Gln Gly Thr Leu Val Thr Val Ser Ser
    130                 135                 140

Ala Ser Gly Gly Gly Gly Ser Gly Gly Gly Gly Ser Gly Gly Gly Gly
145                 150                 155                 160

Ser Gly Gly Gly Asp Thr Pro Met Thr Gln Ser Pro Ser Ser Val Ser
                165                 170                 175

Ala Ser Val Gly Asp Arg Val Thr Ile Ser Cys Arg Ala Ser Gln Gly
            180                 185                 190

Ile Ser Asn Ser Leu Ala Trp Tyr Gln Gln Lys Leu Gly Lys Ala Pro
        195                 200                 205

Gln Leu Leu Ile Tyr Ala Ala Ser Ser Leu Gln Ser Gly Val Pro Ser
    210                 215                 220

Arg Phe Ser Gly Ser Gly Ser Gly Thr Asp Phe Thr Leu Thr Ile Ser
225                 230                 235                 240

Ser Leu Gln Pro Glu Asp Phe Ala Thr Tyr Tyr Cys Gln Gln Thr Asn
```

```
                   245                 250                 255
Thr Phe Pro Phe Thr Phe Gly Pro Gly Thr Lys Val Glu Val Arg Arg
            260                 265                 270

Ala Ser Leu Val Pro Arg Gly Ser Gly Trp Ser His Pro Gln Phe Glu
        275                 280                 285

Lys Gly Gly Ser Gly Gly Ser Gly Gly Ser Trp Ser His
    290                 295                 300

Pro Gln Phe Glu Lys
305

<210> SEQ ID NO 14
<211> LENGTH: 888
<212> TYPE: DNA
<213> ORGANISM: Artificial Sequence
<220> FEATURE:
<223> OTHER INFORMATION: Synthetic Construct

<400> SEQUENCE: 14
atggacgcca tgaagcgggg cctgtgctgt gtgctgctgc tgtgcggagc cgtgttcgtg      60
tcccccagcg aattctcggc aaaccacaaa gtcacaccaa caactgcaat catacaagat    120
gcaacaagcc agatcaagaa cacaaccccca acatacctca cccagaatcc tcagcttgga    180
atcagtccct ctaatccgtc tgaaattaca tcacaaatca ccaccatact agcttcaaca    240
acaccaggag tcaagtcaac cctgcaatcc acaacagtca gaccaagaa cacaacgaca     300 actcaaacac aacccagcaa gcccaccaca aacaacgcc aaaacaaacc accaagcaaa    360
cccaataatg attttcactt tgaagtgttc aactttgtac cctgcagcat atgcagcaac    420
aatccaacct gctgggctat ctgcaaaaga ataccaaaca aaaaccagg aagaaaacc     480 actaccaagc ccacaaaaaa accaacccct caagacaacca aaaagatcc caaacctcaa    540 accactaaat caaggaagt acccaccacc aagcccacag aagagccaac catcaacacc    600
accaaaacaa acatcataac tacactactc acctccaaca ccacaggaaa tccagaactc    660
acaagtcaaa tggaaacctt ccactcaact tcctccgaag gcaatccaag cccttctcaa    720
gtctctacaa catccgagta cccatcacaa ccttcatctc cacccaacac tcctcgccag    780
caccatcacc accatcatgg ttggagtcat ccacaattcg agaagggcgg cggctccgga    840
ggtggatcag gaggtggttc ctggtcacac cctcaattcg agaagtga                 888

<210> SEQ ID NO 15
<211> LENGTH: 138
<212> TYPE: DNA
<213> ORGANISM: Artificial Sequence
<220> FEATURE:
<223> OTHER INFORMATION: Synthetic Construct

<400> SEQUENCE: 15
atgggaaacg acttccactt cgaggtgttc aacttcgttc cgtgcagcat ttgcagcaac     60
aacccgacct gctgggcgat ctgcaaacgt atcccgaaca agaaaccggg taagaaacat    120
caccatcacc atcactga                                                   138

<210> SEQ ID NO 16
<211> LENGTH: 150
<212> TYPE: DNA
<213> ORGANISM: Artificial Sequence
<220> FEATURE:
<223> OTHER INFORMATION: Synthetic Construct

<400> SEQUENCE: 16
```

```
atgggaagca aaccgaacaa cgacttccac ttcgaggtgt tcaacttcgt tccgtgcagc    60
atttgcagca acaacccgac ctgctgggcg atctgcaaac gtatcccgaa caagaaaccg   120
ggtaagaaac atcaccatca ccatcactga                                    150
```

<210> SEQ ID NO 17
<211> LENGTH: 177
<212> TYPE: DNA
<213> ORGANISM: Artificial Sequence
<220> FEATURE:
<223> OTHER INFORMATION: Synthetic Construct

<400> SEQUENCE: 17

```
atgggaacca agcagcgtca gaacaagccg ccgagcaaac cgaacaacga cttccacttc    60
gaggtgttca acttcgttcc gtgcagcatt tgcagcaaca cccgacctg ctgggcgatc   120 tgcaaacgta tcccgaacaa gaaaccgggt aagaaacatc accatcacca tcactga      177
```

<210> SEQ ID NO 18
<211> LENGTH: 132
<212> TYPE: DNA
<213> ORGANISM: Artificial Sequence
<220> FEATURE:
<223> OTHER INFORMATION: Synthetic Construct

<400> SEQUENCE: 18

```
atgggaaacg acttccactt cgaggtgttc aacttcgttc cgtgcagcat ttgcagcaac    60
aacccgacct gctgggcgat ctgcaaacgt atcccgaaca gaaaccggg tcatcaccat   120 caccatcact ga                                                       132
```

<210> SEQ ID NO 19
<211> LENGTH: 909
<212> TYPE: DNA
<213> ORGANISM: Artificial Sequence
<220> FEATURE:
<223> OTHER INFORMATION: Synthetic Construct

<400> SEQUENCE: 19

```
atgaagttat gcatattact ggccgtcgtg gcctttgttg gcctctcgct cgggagatct    60
gaagagcaac tggtggagag cggtggtggt ctggttcagc cgggtcgttc cctgcgtctg   120
tcctgcgtgg gtagcggtct gcgttttgag gagcacgcga tgcactgggt gcgtcaggca   180
ccgggtcgcg gtctggagtg ggtgagcggt atcagctgga acagcggtag cgtgggttat   240
gccgacagcg tgaagggccg tttcaccacc agccgcgaca cgccaagga tatcctgttc   300 ctggagatga acaccctgcg tagcgaggat accgcgctgt acttctgcgc gattatggtg   360
gccaccacca gaacgactt ccactactac aaggatgtgt ggggcaaggg caccaccgtg   420
accgtgagca gtggcggcgg tggcagcggc ggtggcggta gcggtggcgg tggcagccag   480
attgtgctga cccagagccc ggcaaccctg agcctgagcc cggcgagcg tgccaccctg   540 agctgccgtg caagccagag cgtgagcaac cacctggcgt ggtatcagca gaagccgggt   600
caggcgccgc gtctgctgat ctacgaaacc agcaaccgtg ccaccggcat tccgccgcgc   660
ttcagcggca gcgtagcgg caccgacttc accctgacca ttagcagcct ggagccggag   720
gatttcgccg tgtactattg ccaacagcgt aacaactggt acaccttcgg tcagggcacc   780
aaactggaaa tcaaagctag cctggttccc gcggatcgg gttggagtca tccacaattc   840
gagaagggcg gcggctccgg aggtggatca ggaggtggtt cctggtcaca ccctcaattc   900
```

```
gagaagtga                                                               909

<210> SEQ ID NO 20
<211> LENGTH: 930
<212> TYPE: DNA
<213> ORGANISM: Artificial Sequence
<220> FEATURE:
<223> OTHER INFORMATION: Synthetic Construct

<400> SEQUENCE: 20
atgaagttat gcatattact ggccgtcgtg gcctttgttg gcctctcgct cgggagatct        60
caggtgcagc tggtgcagag cggcccggaa gtgaaaaagc cgggcgcaag cgtgcgtctg       120
tcttgcaaag catccggtta cgtgttcacc aactacggtg tgagctgggt gcgccaggct       180
cctggtcagg gcctggaatg gatgggttgg agcagcccat acaacggtaa cacctactat       240
gcgcagaaac tgaaggctcg tgtgaccatg accaccgaca ccagcaccaa caccgcatac       300
atggagctgc gtagcctgcg ctctgacgat accgccgtgt attactgcgg tcgcgatatg       360
ctgggtgtgg tgcaggcagt ggcgggtcca ttcgactcct ggggtcaggg caccctggtg       420
accgtgtcct ctgcaagcgg cggtggtggt tctggtggcg gcggtagcgg tggtggcggt       480
agcggcggcg gtgacacccc aatgacccag tctccgtcct ctgtgtctgc ttccgtgggc       540
gatcgcgtga ccatctcctg ccgcgcatct cagggcatta gcaactctct ggcatggtat       600
cagcagaaac tgggcaaggc tccacagctg ctgatctatg cggcatcctc tctgcagagc       660
ggtgtgcctt ctcgtttctc cggtagcggc tccggcaccg atttcaccct gaccatctcc       720
agcctgcagc cagaggattt cgctacctac tattgccagc agaccaacac cttcccattc       780
accttcggcc ctggcaccaa agtggaagtg cgtcgcgcta gcctggttcc ccgcggatcg       840
ggttggagtc atccacaatt cgagaagggc ggcggctccg gaggtggatc aggaggtggt       900
tcctggtcac accctcaatt cgagaagtga                                       930
```